US008551497B2

(12) United States Patent
Quinn et al.

(10) Patent No.: US 8,551,497 B2
(45) Date of Patent: *Oct. 8, 2013

(54) MICROBIAL VACCINE AND VACCINE VECTOR

(75) Inventors: Frederick Quinn, Avondale Estates, GA (US); Candace McCombs, Athens, GA (US); Russell K. Karls, Athens, GA (US)

(73) Assignee: University of Georgia Research Foundations, Inc., Athens, GA (US)

( * ) Notice: Subject to any disclaimer, the term of this patent is extended or adjusted under 35 U.S.C. 154(b) by 29 days.

This patent is subject to a terminal disclaimer.

(21) Appl. No.: 13/435,484

(22) Filed: Mar. 30, 2012

(65) Prior Publication Data

US 2012/0189657 A1    Jul. 26, 2012

Related U.S. Application Data

(62) Division of application No. 12/095,035, filed as application No. PCT/US2006/046832 on Dec. 8, 2006, now Pat. No. 8,168,421.

(60) Provisional application No. 60/749,140, filed on Dec. 9, 2005, provisional application No. 60/781,303, filed on Mar. 10, 2006.

(51) Int. Cl.
    *A61K 39/04*      (2006.01)

(52) U.S. Cl.
    USPC .............. 424/208.1; 424/209.1; 424/234.1; 424/248.1; 435/69.1; 435/71.1; 435/71.2

(58) Field of Classification Search
    None
    See application file for complete search history.

(56) References Cited

U.S. PATENT DOCUMENTS

| | | | |
|---|---|---|---|
| 4,877,612 A * | 10/1989 | Berger et al. ............. 424/282.1 |
| 5,807,723 A | 9/1998 | Aldovini et al. |
| 6,221,364 B1 | 4/2001 | Pavelka et al. |
| 6,261,568 B1 | 7/2001 | Gicquel et al. |
| 6,270,776 B1 | 8/2001 | Bloom et al. |
| 6,372,478 B1 | 4/2002 | Bloom et al. |
| 7,741,475 B2 | 6/2010 | Fraser-Reid et al. |
| 7,951,565 B2 | 5/2011 | Ebneth et al. |
| 8,168,421 B2 | 5/2012 | Quinn et al. |
| 2003/0236393 A1 | 12/2003 | Trucksis |
| 2005/0014828 A1 | 1/2005 | Murthy et al. |
| 2006/0073167 A1 | 4/2006 | Oshima et al. |
| 2006/0137042 A1 | 6/2006 | Plesch et al. |
| 2008/0015344 A1 | 1/2008 | Fraser-Reid et al. |
| 2008/0107652 A1 | 5/2008 | Durvasula et al. |
| 2012/0258126 A1 * | 10/2012 | Scholler et al. ............ 424/186.1 |

FOREIGN PATENT DOCUMENTS

| | | | |
|---|---|---|---|
| WO | WO 01/19993 A2 | 3/2001 |
| WO | 01/19993 | * 11/2001 |
| WO | WO 01/19993 A3 | 11/2001 |
| WO | WO 2005/014828 A2 | 2/2005 |
| WO | WO 2005/014828 A3 | 7/2005 |
| WO | WO 2007/067729 A2 | 6/2007 |
| WO | WO 2007/067729 A3 | 3/2008 |
| WO | 2012/011144 | * 1/2012 |

OTHER PUBLICATIONS

Rhodes, Mar. 2003, International Journal of Systematic and Evolutionary Microbiology, vol. 53(2), pp. 421-424.*
Rhodes, Mar. 2004, Infection and Immunity, vol. 72(3), pp. 1626-1636.*
Sigma-Aldrich, Certificat of Origin Policy(TSE/BSE), Frequently Asked Questions, Aug. 3, 2005, pp. 1-9.*
Rhodes, Martha W et al, Emerging Infectious Diseases, vol. 7(5), Sep.-Oct. 2001, pp. 896-899.*
U.S. Appl. No. 60/749,140, filed Dec. 9, 2005, Quinn et al.
U.S. Appl. No. 60/781,303, filed Mar. 10, 2006, Quinn et al.
Abramson, "Intranasal, cold-adapted, live, attenuated influenza vaccine," *Pediatr. Infect. Dis. J.*, Dec. 1999; 18(12):1103-4.
Aldovini et al., "Humoral and cell-mediated immune responses to live recombinant BCG-HIV vaccines," *Nature*, Jun. 6, 1991; 351(6326):479-482.
Asanuma et al., "Isolation and characterization of mouse nasal-associated lymphoid tissue," *J. Immunol. Methods*, 1997; 202(2):123-31.
Bardiya et al., "Influenza vaccines: recent advances in production technologies," *Applied Microbiology and Biotechnology*, 2005; 67(3):299-305.
Barletta et al., "Recombinant BCG as a candidate oral vaccine vector," *Research in Microbiology*, Sep.-Oct. 1990; 141(7-8):931-939.
Barnett, "Influenza Immunization for Children," *New England Journal of Medicine*, 1998; 338(20):1459-1461.
Barry et al., "Immune responses elicited against multiple enterotoxigenic *Escherichia coli* fimbriae and mutant LT expressed in attenuated *Shigella* vaccine strains," *Vaccine*, Jan. 2003; 21(5-6):333-340.
Beggs, et al. "Isolation and Sequencing of the Replication Region of *Mycobacterium avium* Plasmid pLR7" 1995. *Journal of Bacteriology*. 177(17):4836-4840.

(Continued)

*Primary Examiner* — Albert Navarro
*Assistant Examiner* — Ginny Portner
(74) *Attorney, Agent, or Firm* — Mueting Raasch & Gebhardt, P.A.

(57) ABSTRACT

The present invention includes cold-adapted, acid-fast bacterium for use as a vaccine and a vaccine vector. In preferred embodiments, the cold-adapted, acid-fast bacterium is a *Mycobacteria*, for example, *Mycobacteria shottsii*.

23 Claims, No Drawings

(56) References Cited

OTHER PUBLICATIONS

Belsche et al., "The Efficacy of Live Attenuated, Cold-Adapted, Trivalent, Intranasal Influenzavirus Vaccine in Children," *The New England Journal of Medicine*, May 14, 1998; 338(20):1405-1412.

Belsche, "Current status of live attenuated influenza virus vaccine in the US," *Virus Research*, Jul. 2004; 103(1-2):177-185.

Besnard et al., "Bacillus Calmette-Guérin infection after vaccination of human immunodeficiency virus-infected children," *Pediatr Infect Dis J*, 1993; 12(12):993-997.

Birkness et al., "An in vitro model of the leukocyte interactions associated with granuloma formation in *Mycobacterium tuberculosis* infection," *Immunol. Cell Biol.*, Jan. 2, 2007; 85:160-168.

Bland et al., "Statistics Notes: Survival probabilities (the Kaplan-Meier method)," *BMJ*, Dec. 1998; 317:1572.

Bland et al., "Statistics Notes: The logrank test," *BMJ*, May 1, 2004; 328:1073. Correction published Jun. 12, 2004; 328:1412.

Brennan et al., "Global Forum on TB Vaccine Research and Development. World Health Organization, Jun. 7-8 2001, Geneva," *Tuberculosis*, 2001; 81(5/6):365-368.

Brennan et al., "Tuberculosis vaccine development: research, regulatory and clinical strategies," *Expert Opinion on Biological Therapy*, Sep. 2004; 4(9):1493-1504.

Brennan et al., "The tuberculosis vaccine challenge," *Tuberculosis*, Jan.-Mar. 2005; 85(1-2):7-12.

Brigl et al., "CD1: Antigen Presentation and T Cell Function," *Annual Review of Immunology*, Apr. 2004; 22:817-890.

Brown, "The epidemiology and evolution of influenza viruses in pigs," *Veterinary Microbiology*, May 22, 2000; 74(1-2):29-46.

Burge et al., "*Mycobacterium*-inducible *Nramp* in striped bass (*Morone saxatilis*)," *Infection and Immunity*, 2004; 72(3):1626-1636.

Butler et al., "Mycolic Acid Analysis by High-Performance Liquid Chromatography for Identification of *Mycobacterium* Species," *Clinical Microbiology Reviews*, Oct. 2001; 14(4):704-726.

Castañón-Arreola et al., "A second-generation anti TB vaccine is long overdue," *Ann. Clin. Microbiol. Antimicrob.*, 2004; 3(1):10.

Chen et al., "Single Intranasal Mucosal *Mycobacterium bovis* BCG Vaccination Confers Improved Protection Compared to Subcutaneous Vaccination against Pulmonary Tuberculosis," *Infection and Immunity*, Jan. 2004; 72(1):238-46.

Copenhaver et al., "A Mutant of *Myobacterium tuberculosis* H37Rv That Lacks Expression of Antigen 85A Is Attenuated in Mice but Retains Vaccinogenic Potential," *Infection and Immunity*, 2004; 72(12):7084-7095.

Corbett et al., "The Growing Burden of Tuberculosis: Global Trends and Interactions With the HIV Epidemic," *Arch. Intern. Med.*, 2003; 163(9):1009-1021.

Cox et al., "Influenza virus: immunity and vaccination strategies. Comparison of the immune response to inactivated and live, attenuated influenza vaccines," *Scand. J. Immunol.*, Jan. 2004; 59(1):1-15.

Culshaw et al., "Gut Intraepithelial Lymphocytes Induce Immunity against *Cryptosporidium* Infection through a Mechanism Involving Gamma Interferon Production," *Infection and Immunity*, Aug. 1997; 65(8):3074-3079.

Dascher et al., "Immunization with a mycobacterial lipid vaccine improves pulmonary pathology in the guinea pig model of tuberculosis," *International Immunology*, Aug. 2003; 15(8):915-925.

Dascher et al., "CD1 and Tuberculosis," Ch. 30 of *Tuberculosis and the Tubercle Bacillus*, Washington, D.C. 2005, pp. 475-488.

Davis, "Nasal vaccines," *Advanced Drug Delivery Reviews*, Sep. 2001; 51(1-3):21-42.

Dieli et al., "Characterization of Lung γδ T Cells Following Intranasal Infection with *Mycobacterium bovis* Bacillus Calmette-Guérin," *The Journal of Immunology*, 2003; 170(1):463-469.

Drandarska et al., "Combined immunomodulating effects of BCG and Lentinan after intranasal application in guinea pigs," *International Immunopharmacology*, Apr. 2005; 5(4):795-803.

Dupuy et al., "Nasal Immunization of Mice with Human Papillomavirus Type 16 (HPV-16) Virus-Like Particles or with the HPV-16 L1 Gene Elicits Specific Cytotoxic T Lymphocytes in Vaginal Draining Lymph Nodes," *J. Virol.*, 1999; 73(11):9063-9071.

Dye et al., "Evolution of Tuberculosis Control and Prospects for Reducing Tuberculosis Incidence, Prevalence, and Deaths Globally," *JAMA*, 2005; 293(22):2767-2775.

Falero-Diaz et al., "Intranasal vaccination of mice against infection with *Mycobacterium tuberculosis*," *Vaccine*, Aug. 2000; 18(28):3223-3229.

Flynn, "Immunology of tuberculosis and implications in vaccine development," *Tuberculosis*, 2004; 84(1-2):93-101.

Fuerst et al., "Development of BCG as a live recombinant vector system: potential use as an HIV vaccine," *Biotechnol. Ther.*, 1991; 2(1-2):159-178.

Gaulthier et al., "Experimental mycobacteriosis in striped bass *Morone saxatilis*," *Dis. Aquat. Organ.*, 2003; 54(2):105-117.

Giquel, "Towards new mycobacterial vaccines," *Developments in Biological Standardization*, 1994; 82:171-178.

Goonetilleke et al., "Enhanced Immunogenicity and Protective Efficacy Against *Mycobacterium tuberculosis* of Bacille Calmette-Guérin Vaccine Using Mucosal Administration and Boosting with a Recombinant Modified Vaccinia Virus Ankara," *J. Immunol.*, 2003; 171(3):1602-1609.

Hesseling et al., "Danish Bacille Camette-Guérin Vaccine-Induced Disease in Human Immunodeficiency Virus-Infected Children," *Clinical Infectious Diseases*, 2003; 37(9):1226-33. Erratum in: *Clinical Infectious Diseases*, 2003; 37(12):1727.

Hiromatsu, et al., "Induction of CD1-Restricted Immune Responses in Guinea Pigs by Immunization with Mycobacterial Lipid Antigens," *J. Immunol.*, Jul. 1, 2002; 169(1):330-9.

Horwitz et al., "Enhancing the Protective Efficacy of *Mycobacterium bovis* BCG Vaccination against Tuberculosis by Boosting with the *Mycobacterium tuberculosis* Major Secretory Protein," *Infection and Immunity*, Aug. 2005; 73(8):4676-4683.

Hunger et al., "Langerhans cells utilize CD1a and langerin to efficiently present nonpeptide antigens to T cells," *J. Clin. Invest.*, Mar. 2004; 113(5):701-708.

Hussey et al., "Neonatal mycobacterial specific cytotoxic T-lymphocyte and cytokine profiles in response to distinct BCG vaccination strategies," *Immunology*, 2002; 105(3):314-324.

Illum et al., "Nasal vaccination: a non-invasive delivery method that holds great promise for the future," *Advanced Drug Delivery Reviews*, Sep. 2001; 51(1-3):1-3.

Kamath et al., "New live mycobacterial vaccines: the Geneva consensus on essential steps towards clinical development," *Vaccine*, May 2005; 23(29):3753-3761.

Kanekiyo et al., "Mycobacterial Codon Optimization Enhances Antigen Expression and Virus-Specific Immune Responses in Recombinant *Mycobacterium bovis* Bacille Calmette-Guérin Expressing Human Immunodeficiency Virus Type 1 Gag," *Journal of Virology*, Jul. 2005; 79(14):8716-8723.
Karls et al., "Examination of *Mycobacterium tuberculosis* sigma factor mutants using low-dose aerosol infection of guinea pigs suggests a role for SigC in pathogenesis," *Microbiology*, 2006; 152:1591-1600.
Kemble et al., "Novel generations of influenza vaccines," *Vaccine*, May 2003; 21(16):1789-1795.
Kida et al., "Biological activity of monoclonal antibodies to operationally defined antigenic regions on the hemagglutinin molecule of A/Seal/Massachusetts/1/80 (H7N7) influenza virus," *Virology*, Oct. 15, 1982; 122(1):38-47.
King et al., "Safety and immunogenicity of low and high doses of trivalent live cold-adapted influenza vaccine administered intranasally as drops or spray to healthy children," *J. Infect. Dis.*, May 1998; 177(5):1394-1397.
Kyd et al., "Mucosal immunity in the lung and upper airway," *Vaccine*, Mar. 2001; 19(17-19):2527-2533.
Lagranderie et al., "Dendritic cells recruited to the lung shortly after intranasal delivery of *Mycobacterium bovis* BCG drive the primary immune response towards a type 1 cytokine production," *Immunology*, 2003; 108(3):352-364.
Lasco et al., "Evaluating the role of tumor necrosis factor-alpha in experimental pulmonary tuberculosis in the guinea pig," *Tuberculosis (Edinb.)*, 2005; 85(4):245-258.

(56) References Cited

OTHER PUBLICATIONS

Liang et al., "Heterosubtypic immunity to influenza type a virus in mice: Effector mechanisms and their longevity," *J. Immunol.*, 1994; 152:1653-1661.
Lim, et al., "Mucosal vaccination against influenza: protection of pigs immunized with inactivated virus and ether-split vaccine," *Jpn. J. Vet. Res.*, Feb. 2001; 48(4):197-203.
Liu, "Dendritic Cell Subsets and Lineages, and Their Functions in Innate and Adaptive Immunity," *Cell*, 2001; 106(3):259-262.
Lyadova et al., "Intranasal BCG vaccination protects BALB/c mice against virulent *Mycobacterium bovis* and accelerates production of IFN-γ in their lungs," *Clinical Exp. Immunol.*, 2001; 126(2):274-279.
Maassab et al., "Development and characterization of cold-adapted viruses for use as live virus vaccines," *Vaccine*, Dec. 1985; 3(5):355-369.
Manssab et al., "The development of live attenuated cold-adapted influenza virus vaccine for humans," Reviews in Medical Virology, Oct./Dec. 1999; 9(4):237-244.
McMurray, "Recent progress in the development and testing of vaccines against human tuberculosis," *Int. Journal for Parasitology*, May 2003; 33(5-6):547-554.
MedImmune Vaccines, "Influenza virus vaccine live intranasal—MedImmune vaccines: CAIV-T, influenza vaccine live intranasal," *Drugs R D*, 2003; 4(5):312-319.
Mehta et al., "Entry and intracellular replication of *Mycobacterium tuberculosis* in cultured human microvascular endothelial cells," *Microb. Path.*, 2006; 41:119-124.
Miltner et al. "Identification of *Mycobacterium avium* Genes That Affect Invasion of the Intestinal Epithelium" 2005. *Infection and Immunity*. 73(7):4214-4221).
Murray, "A Century of Tuberculosis," *Am. J. Respir. Crit. Care Med.*, 2004; 169:1181-1186.
Moody et al., "Intracellular pathways of CD1 antigen presentation," *Nature Reviews Immunology*, Jan. 2003; 3(1):11-22.
Mve-Obiang et al., "A Newly Discovered Mycobacterial Pathogen Isolated from Laboratory Colonies of *Xenopus* Species with Lethal Infections Produces a Novel Form of Mycolactone, the *Mycobacterium ulcerans* Macrolide Toxin," *Infection and Immunity*, Jun. 2005; 73(6):3307-3312.
National Center for Biotechnology Information, National Library of Medicine, National Institutes of Health, GenBank Locus AY496288, Accession No. AY496288, "*Mycobacterium shottsii* strain M175 cell wall-associated protein (erp) gene, partial cds," [online]. Bethesda, MD [retrieved on Jun. 26, 2008]. Retrieved from the Internet: 2 pgs.
NIAID News, "Nasal Spray Vaccine Prevents Both the Flu and Flu-Related Earaches," May 13, 1998 [retrieved on Jun. 25, 2008]. Retrieved from the Internet: 5 pgs.
Nor et al., "Approaches towards the development of a vaccine against tuberculosis: recombinant BCG and DNA vaccine," Tuberculosis; 2004; 84(1-2):102-9.
Nuermberger et al., "Paucibacillary Tuberculosis in Mice after Prior Aerosol Immunization with *Mycobacterium bovis* BCG," *Infection and Immunity*, Feb. 2004; 72(2):1065-1071.
Palese, "Making Better Influenza Virus Vaccines'?" *Emerging Infectious Diseases*, Jan. 2006; 12(1):61-65.
Pasetti et al., "Attenuated *Salmonella enterica* Serovar Typhi and *Shigella flexneri* 2a Strains Mucosally Deliver DNA Vaccines Encoding Measles Virus Hemagglutinin, Inducing Specific Immune Responses and Protection in Cotton Rats," *Journal of Virology*, May 2003; 77(9):5209-5217.
Patel, "Evaluation of a quadrivalent inactivated vaccine for the protection of cattle against diseases due to common viral infections," *J. S. Afr. Vet. Assoc.*, Sep. 2004; 75(3):137-46.
Peña-Cruz et al., "Epidermal Langerhans Cells Efficiently Mediate CD1a-Dependent Presentation of Microbial Lipid Antigens to T Cells," *J. Invest. Dermatol.*, 2003; 121(3):517-521.
Porgador et al., "Intranasal Immunization with Cytotoxic T-Lymphocyte Epitope Peptide and Mucosal Adjuvant Cholera Toxin: Selective Augmentation of Peptide-Presenting Dendritic Cells in Nasal Mucosa-Associated Lymphoid Tissue," *Infection and Immunity*, Dec. 1998; 66(12):5876-5881.
Posey et al., "Characterization of the Twin-Arginine Translocase Secretion System of *Mycobacterium smegmatis*," *Journal of Bacteriology*, Feb. 2006; 188(4):1332-1340.
Reljic et al., "Time course of mycobacterium infection of dendritic cells in the lungs of intranasally infected mice," *Tuberculosis*; Jan.-Mar. 2005; 85(1-2):81-88.
Rhodes et al., "A Unique *Mycobacterium* Species Isolated from an Epizootic of Striped Bass (*Morone saxatilis*)," *Emerging Infectious Diseases*, Sep.-Oct. 2001; 7(5):896-899.
Rhodes et al., "*Mycobacterium shottsii* sp. nov., a slowly growing species isolated from Chesapeake Bay striped bass (*Morone saxatilis*)," *International Journal of Systematic and Evolutionary Microbiology*, 2003; 53(2):421-424. Available online on Aug. 16, 2002.
Rhodes et al., "*Mycobacterium pseudoshottsii* sp. nov., a slowly growing chromogenic species isolated from Chesapeake Bay striped bass (*Morone saxatilis*)," *International Journal of Systematic and Evolutionary Microbiology*, 2005; 55(3):1139-1147.
Sambandamurthy et al., "A pantothenate auxotroph of *Mycobacterium tuberculosis* is highly attenuated and protects mice against tuberculosis," *Nature Medicine*, Oct. 2002; 8(10):1171-1174.
Sampson et al., "Protection Elicited by a Double Leucine and Pantothenate Auxotroph of *Mycobacterium tuberculosis* in Guinea Pigs," *Infection and Immunity*, May 2004; 72(5):3031-3037.
Santosuosso et al., "Mechanisms of Mucosal and Parenteral Tuberculosis Vaccinations: Adenoviral-Based Mucosal Immunization Preferentially Elicits Sustained Accumulation of Immune Protective CD4 and CD8 Cells within the Airway Lumen," *The Journal of Immunology*, 2005; 174(12):7986-7994.
Schwartz et al., "Vaccination Strategies for an Influenza Pandemic," *JID*, Apr. 2005; 191:1207-1209.
Sieling et al., The Human CD1-Restricted T Cell Repertoire Is Limited to Cross-Reactive Antigens: Implications for Host Responses against Immunologically Related Pathogens, *J Immunol.*, Mar. 1, 2005; 174(5):2637-44.
Singh et al. "Influence of *Mycobacterium avium* subsp. *paratuberculosis* on Colitis Development and Specific Immune Responses during Disease" 2007. *Infection and Immunity*. 75(8):3722-3728.
Stover et al., "New use of BCG for recombinant vaccines," *Nature*, Jun. 1991; 351(6326):456-460.
Straszek et al., "Nasal cavity dimensions in guinea pig and rat measured by acoustic rhinometry and fluid-displacement method," *J. Appl. Physiol.*, Feb. 2004; 96:2109-2114.
Takada et al., "Intranasal immunization with formalin-inactivated virus vaccine induces a broad spectrum of heterosubtypic immunity against influenza A virus infection in mice," *Vaccine*, Jul. 2003; 21(23):3212-3218.
Talbot et al., "Disseminated Bacille Calmette-Guérin Disease After Vaccination: Case Report and Review," *Clinical Infectious Diseases*, 1997; 24:1139-46.
Tamura et al., "Mechanisms of Broad Cross-Protection Provided by Influenza Virus Infection and Their Application to Vaccines," *Jpn. J. Infect. Dis.*, 2005; 58:195-207.
Tortoli, "Impact of Genotypic Studies on Mycobacterial Taxonomy: the New Mycobacteria of the 1990s," *Clinical Microbiology Reviews*, Apr. 2003; 16(2):319-354.
Tree et al., "Intranasal bacille Calmette-Guérin (BCG) vaccine dosage needs balancing between protection and lung pathology," *Clin. Exp. Immunol.*, Dec. 2004; 138(3):405-409.
Tsien, "The Green Fluorescent Protein," *Annual Review of Biochemistry*, Jul. 1998; 67:509-544.
Ulrichs et al., "T-Cell Responses to CD1-Presented Lipid Antigens in Humans with *Mycobacterium tuberculosis* Infection," *Infect. Immun.*, 2003; 71(6):3076-3087.
Wang et al., "Single Mucosal, but Not Parenteral, Immunization with Recombinant Adenoviral-Based Vaccine Provides Potent Protection from Pulmonary Tuberculosis," *J Immunol.*, 2004; 173(10):6357-65.

(56) References Cited

OTHER PUBLICATIONS

Winter et al., "Expression of heterologous genes in *Mycobacterium bovis* BCG: induction of a cellular response against HIV-1 Nef protein," *Gene*, Dec. 1991; 109(1):47-54.

Wu et al., "Generation of Female Genital Tract Antibody Responses by Local or Central (Common) Mucosal Immunization," *Infection and Immunity*, Oct. 2000; 68(10):5539-5545.

Wuethrich, "Chasing the Fickle Swine Flu," *Science*, Mar. 7, 2003; 299(5612):1502.

Ze et al., "Identification of Effective Constituents of Influenza Vaccine by Immunization with Plasmid DNAs Encoding Viral Proteins," *Jpn. J. Infect. Dis.*, 2000; 53:219-228.

Zhao et al., "Symptomatic and pathophysiological observations in a modified animal model of allergic rhinitis," *Rhinology*, 2005; 43(1):47-54.

Zuercher et al., "Nasal-Associated Lymphoid Tissue Is a Mucosal Inductive Site for Virus-Specific Humoral and Cellular Immune Responses," *J. Immunol.*, 2002; 168(4):1796-1803.

International Search Report and Written Opinion mailed on Feb. 4, 2008, in regard to International Application No. PCT/US2006/046832, filed on Dec. 8, 2006 (7 pgs).

International Preliminary Report on Patentability issued on Jun. 11, 2008, in regard to International Application No. PCT/US2006/046832, filed on Dec. 8, 2006 (5 pgs).

\* cited by examiner

MICROBIAL VACCINE AND VACCINE VECTOR

This application is a divisional application of U.S. Ser. No. 12/095,035, filed on Sep. 26, 2008, which is a 371 of PCT/US06/46832 filed on Dec. 8, 2006, which claims the benefit of U.S. Provisional Application Ser. No. 60/749,140, filed Dec. 9, 2005, and U.S. Provisional Application Ser. No. 60/781,303, filed Mar. 10, 2006, all of which are incorporated by reference herein.

BACKGROUND

There are many infectious diseases for which an effective vaccine has not yet been developed, and many of the currently available vaccines provide only partial protection against disease. Further, there are gaps in the vaccine field. Live vaccines produce stronger, broader, and more durable immunity than other types of vaccines. There is a need for a safer live vaccine vehicle, which will be unable to cause disease even in immunosuppressed individuals. There is also a need for vaccines that induce cell-mediated immunity and not just antibody-based immunity. And, there is a need to induce protective immune responses directly at the mucosal surfaces of the body, where most pathogens gain entry. Thus, there is a need for improved vaccines.

SUMMARY OF THE INVENTION

The present invention includes a pharmaceutical composition including an acid-fast bacterium with a maximum survival temperature of 30° C. and a pharmaceutically acceptable carrier. In some embodiments, the acid-fast bacterium with a maximum survival temperature of 30° C. is *Mycobacterium shottsii*, *Mycobacterium pseudoshottsii*, or *Mycobacterium liflandii*.

The present invention also includes a pharmaceutical composition including *Mycobacterium shottsii* and a pharmaceutically acceptable carrier.

The present invention also includes a pharmaceutical composition including a transgenic *M. shottsii* with at least one heterologous antigen and/or immunogen; and a pharmaceutically acceptable carrier. In some embodiments, at least one heterologous antigen and/or immunogen includes a human immunodeficiency (HIV) virus antigen and/or immunogen. In some embodiments, at least one heterologous antigen and/or immunogen includes a *Mycobacterium tuberculosis* antigen and/or immunogen. In some embodiments, at least one heterologous antigen and/or immunogen includes an influenza virus antigen and/or immunogen. In some embodiments, the influenza virus antigen or immunogen includes a hemaglutinin (HA) antigen or immunogen. In some embodiments, the influenza virus infects humans or swine. In some embodiments, the transgenic *M. shottsii* includes a plurality of heterologous antigens and/or immunogens.

In some embodiments, a pharmaceutical composition of the present invention further includes an adjuvant. In some embodiments, a pharmaceutical composition of the present invention is formulated for administration to the mucosa. In some embodiments, a pharmaceutical composition of the present invention is formulated for intranasal administration.

Also included in the present invention is a transgenic *M. shottsii*, wherein the transgenic *M. shottsii* includes at least one heterologous antigen and/or immunogen.

In some embodiments, at least one heterologous antigen and/or immunogen includes a human immunodeficiency (HIV) virus antigen and/or immunogen. In some embodiments, at least one heterologous antigen and/or immunogen includes a *Mycobacterium tuberculosis* antigen and/or immunogen. In some embodiments, at least one heterologous antigen and/or immunogen includes an influenza virus antigen and/or immunogen. In some embodiments, the influenza virus antigen or immunogen includes a hemaglutinin (HA) antigen or immunogen. In some embodiments, the influenza virus infects humans or swine. In some embodiments, the transgenic *M. shottsii* includes a plurality of heterologous antigens and/or immunogens Also included in the present invention are methods of treating or preventing tuberculosis in a mammalian subject by administering a transgenic *M. shottsii* of the present invention or a pharmaceutical composition of the present invention.

Also included in the present invention are methods of inducing an immune response to an antigen or immunogen in a subject by administering to the subject a transgenic *M. shottsii* of the present invention or a pharmaceutical composition of the present invention.

Also included in the present invention are methods of treating or preventing at least one of a human immunodeficiency virus (HIV) infection, an opportunistic infection or a disease that co-occurs with HIV infection by administering a transgenic *M. shottsii* of the present invention or a pharmaceutical composition of the present invention.

Also included in the present invention are methods of treating or preventing influenza by administering a transgenic *M. shottsii* of the present invention or a pharmaceutical composition of the present invention.

In some embodiments of the methods of the present invention, the transgenic *M. shottsii* or the pharmaceutical composition is administered to the subject's mucosa. In some embodiments of the methods of the present invention, the transgenic *M. shottsii* or the pharmaceutical composition is administered intranasally. In some embodiments of the methods of the present invention, the transgenic *M. shottsii* or the pharmaceutical composition induces an immune response in genital tissue of the subject. In some embodiments of the methods of the present invention, the subject is immunocompromised.

Unless otherwise specified, "a," "an," "the," and "at least one" are used interchangeably and mean one or more than one.

DETAILED DESCRIPTION OF ILLUSTRATIVE EMBODIMENTS OF THE INVENTION

The present invention provides improved vaccines and vaccine vectors. With the present invention, a cold-adapted, acid-fast bacterium is used as a vaccine and a vaccine vector. In preferred embodiments, the cold-adapted, acid-fast bacterium is a *Mycobacteria*, for example, *Mycobacteria shottsii*.

As used herein, acid-fast bacteria have an acid-fast cell wall that resist decolorization with an acid-alcohol mixture during the acid-fast stain procedure, retaining the initial dye carbol fuchsin and appearing red when viewed under the light microscope. Examples of acid-fast staining procedures include, but are not limited to, Kinyoun carbolfuchisin staining and Ziehl-Neelson staining.

As used herein, cold-adapted bacteria include bacteria that show a limited ability to survive at 37° C. and/or an inability to grow at 37° C. Cold-adapted bacteria include bacteria with a maximum survival temperature of about 30° C. Cold-adapted bacteria include bacteria that grow best at a temperature of about 22° C. to about 26° C. and do not grow at a temperature of about 37° C. Cold-adapted bacteria include bacteria that grow best at a temperature of about 23° C. to about 25° C. and do not grow at a temperature of about 37° C. Cold-adapted bacteria may survive culture at room temperature. Cold-adapted bacteria include bacteria that grow best at a temperature of about 23° C., at about 24° C., at about 24° C., or about 25° C. Cold-adapted means that a microbe can replicate at a colder than normal temperature, whereas temperature-sensitive means that replication is substantially reduced or eliminated at a higher temperature (Belshe, Virus Res. 2004; 103(1-2):177-85).

Cold-adapted, acid-fast bacteria include, for example, various species of *Mycobacterium*, various species of *Nocardia*, and various species of *Corynebacterium*. Cold-adapted, acid-fast species of *Mycobacterium* may include, but are not limited to, *M. shottsii, M. pseudoshottsii,* and *M. liflandli*. In some embodiments, the cold-adapted bacteria is not *M. bovis*, is not *M. tuberculosis*, and/or is not *M. leprae*. In a preferred embodiment, the cold-adapted bacteria is *M. shottsii*.

*M. shotsii* is a bacteria isolated from striped bass in the Chesapeake Bay, and identified as a new species in 2001 (Rhodes et al., Emerg Infect Dis. 2001; 7(5):896-9; Rhodes et al., Int J Syst Evol Microbiol. 2003; 53(Pt 2):421-4). Based upon genetic and lipid analysis, it is considered to be phylogenetically closely related to members of the *Mycobacterium tuberculosis* complex, a grouping that includes the attenuated live vaccine vector BCG. BCG has long been used in its native form as a vaccine against tuberculosis and leprosy, both diseases caused by mycobacteria. Importantly, BCG has been shown experimentally to be able to act as a vaccine vector. That is to say, it is able to induce protective immunity against diseases caused by unrelated pathogens when BCG genetically engineered to express antigens form those pathogens has been used as a vaccine. While vaccination with live BCG mycobacteria rarely causes disease in people with healthy immune systems, it can cause serious pathology, disseminated disease, and even death in subjects whose immune systems have been compromised by HIV infection, chemotherapy, immunosuppressive drugs, or a number of other circumstances.

A cold-adapted, acid-fast bacteria may serve as a vaccine and a vaccine vector for any of the uses as described herein. For example, a cold-adapted, acid-fast bacteria may serve as a vaccine useful to treat or prevent tuberculosis, including multidrug resistant (MDR) tuberculosis. A cold-adapted, acid-fast bacteria may, for example, serve as a vaccine vector useful to treat or prevent human immunodeficiency virus (HIV) infection, influenza, an opportunistic infection, or a disease that co-occurs with HIV infection. A cold-adapted, acid-fast bacteria may, for example, serve as a vaccine or vaccine vector useful to treat or prevent a cancer. A cold-adapted, acid-fast bacteria may, for example, serve as a vaccine or vaccine vector useful to treat or prevent a veterinary disease or cancer.

The present invention includes a cold-adapted bacteria, such as, for example, *M. shotsii*, genetically engineered to express one or more antigens or immunogens from another organism, such as an infectious pathogen. A cold adapted bacteria can not grow at mammalian internal body temperature, (which is 37 degrees Celsius in humans). In fact, attempts to cultivate *M. shotsii* at temperatures of 30 degrees or above have been uniformly unsuccessful. Such temperature restricted growth make cold-adapted bacteria, such as *M. shotsii*, unable to cause a disseminated infection in mammals, and thus, make it substantially safer as a vaccine or as a vaccine vector. Because the organism cannot grow at body temperature, it can be used, for example, a nasal vaccine, where its growth or persistence is limited to the cooler superficial tissues of the nose and upper airways. Cold-adapted bacteria, including *M. shottsii*, will be especially useful as intranasal vaccines.

Cold-adaptation of viruses is a proven attenuation strategy for intranasal vaccines. Several cold-adapted intranasal viral vaccines for veterinary uses are in clinical use, and more are under development. A number of cold-adapted vaccines for human use are under development, including intranasal vaccines for respiratory syncytial virus (RSV), one of which is already in clinical trials, and a cold-adapted vaccine for PIV3. Already in clinical use is the cold-adapted influenza vaccine FluMist®. FluMist® combines three strains of influenza viruses, each of which is cold-adapted as well as temperature-sensitive.

Human influenza virus strains that have been purposefully adapted to grow at 25° C., but not at 37° C. farm the basis of the FluMist® intranasal flu vaccine (NIAID NEWS, "Nasal spray vaccine prevents both the flu and flu-related earaches," available on the world wide web at niaid.nih.gov; and Maassab and Bryant, Rev Med. Virol. 1999; 9(4):237-44). The temperature growth limitations of such influenza strains allow replication in the superficial tissues of the upper respiratory passages, but prevent penetration deeper into the tissues or lower into the respiratory tract. Cold-adaptation is a key mechanism of attenuation that allows them to be used as vaccines. The cold-adaptation of the viral strains allows them to persist and replicate in the superficial nasopharyngeal tissues, at least until the host immune response eliminates them. This pattern of persistence and growth mimics a natural infection and produces a strong and durable immune memory response (Bardiya and Bae, Appl Microbiol Biotechnol. 2005; 67(3):299-305). As recently reported, the FluMist® vaccine provided 93% protection against the flu and, unexpectedly, 98% protection against a common complication of the flu in children, otitis media (Belshe et al., N Engl J. Med. 1998; 338(20):1405-12; and Barnett, N Engl J. Med. 1998; 338(20):1459-61). The temperature restriction of FluMist® viral strains resembles that of *M. shotsii*, indicating that *M. shotsii*, both in its native form or engineered to express antigens from other pathogens can be used as live nasal vaccines. While other viruses are being cold-adapted for use as nasal vaccines, a cold-adapted live bacteria has never been used as a vaccine or vaccine vector.

With the present invention, native or genetically engineered cold-adapted bacteria, including *M. shottsii*, can be used as effective and safe vaccines for the treatment and prevention of diseases caused by mycobacteria, including, but not limited to, tuberculosis, leprosy, *M. ulcerans* disease, Johnes disease, and opportunistic infections caused by M aviun or other nontuberculous mycobacteria. With the present invention, native or genetically engineered cold-adapted bacteria, including *M. shottsii*, can be used as effective and safe vaccines for the treatment and prevention of tuberculosis, including multi-drug resistant (MDR) tuberculosis. Genetic modifications include, for example, those that further attenuate *M. shottsii* and/or those that introduce one or more transgenes.

With the present invention, native or genetically engineered cold-adapted bacteria, including *M. shottsii*, can be used as effective and safe vaccines for the treatment and prevention a variety of diseases, including, but not limited to, influenza, HIV, malaria, schistosomiasis, *Chlamydia*, mycoplasma, SARS, RSV, measles, Lyme disease, pneumococcal pneumonia, hepatitis B, and pneumonia caused by human metapneumovirus in variety of subjects. Subjects include, but are not limited to, humans, primates, swine, horses, cattle, chickens, turkeys, dogs, cats, and other livestock and domestic pets.

With the present invention, native or genetically engineered cold-adapted bacteria, including *M. shotsii*, can be used as effective and safe vaccines for the treatment and prevention a variety of cancers.

The present invention includes *M. shottsii* genetically modified to express one or more foreign antigens or immunogens. As used herein a foreign antigen or immunogen is a polypeptide that is heterologous with respect to *M. shottsii*. A genetically modified *M. shottsii* is a transgenic *M. shottsi* it includes one or more transgenes that function as, or encode, a foreign antigen or immunogen. Foreign antigens and/or immunogens can take the faun of, for example, polynucleotides such as a DNA or RNA, as well as polypeptides. Foreign antigens or immunogens are preferably derived from a pathogenic organism, and can be, for example, viral or bacterial in origin, or obtained from a pathogenic protozoan or helminth. Optionally, the genetically modified *M. shottsii* includes genetic modifications that further attenuate *M. shottsii*.

Transgenic vaccine vector constructs may be include all or only a portion of the genome of the pathogen. If only a portion of the pathogen's genome is included, the transgenic vector preferably encodes, for example, immunogenic or immunostimulatory proteins or protein fragments. For example, in a preferred embodiment of a transgenic vaccine vector useful to treat or prevent influenza, the construct may include an influenza hemagglutinin (HA) gene, or a portion thereof. Promoters and signal sequences may be varied and codon usage may be optimizing for synthesis in mycobacteria.

Engineered cold-adapted bacteria of the present invention, include bacteria engineered to express foreign antigens from influenza, HIV, malaria, schistosomiasis, *Chlamydia*, mycoplasma, SARS, RSV, measles, pneumonia caused by human metapneumovirus, Lyme diseae, pneumococcal pneumonia, hepatitis B, and other pathogens or cancer antigens, using previously described methods or any of the methods described herein. See, for example, Barletta et al., Res Microbiol. 1990; 141(7-8):931-9; Fuerst et al., Biotechnol Ther. 1991; 2(1-2):159-78; Stover et al., Nature. 1991 Jun. 6; 351 (6326):456-60; Aldovini and Young, Nature. 1991 Jun. 6; 351(6326):479-82; and Winter et al., Gene. 1991 Dec. 20; 109(1):47-59; Barletta et al., Res Microbiol. 1990; 141:931-9; Fuerst et al., Biotechnol Ther. 1991; 2(1-2):159-78; Stover et al., Nature 1991; 351(6326):456-60; Aldovini and Young, Nature 1991; 351(6326):479-82; and Winter et al., Gene. 1991; 109:47-59).

A wide variety of systems for the introduction and expression of foreign genes into *M. shottsii* are available, including, but not limited to, any of those described herein. For example, a shuttle plasmid vector, that replicates extrachromosomally and carries 20 kb or more of foreign genetic material, or a shuttle phasmid vectors, that stably integrates into the mycobacterial chromosome along with large amounts of foreign DNA, can be used. By selecting various leader sequences or even by inserting foreign DNA into the sequence of a mycobacterial gene, it is possible to direct the expressed protein to the cell membrane, or to remain in the cytoplasm, or to be exported from the cell. Furthermore, a large number of native or foreign promoters are available to drive the expression of foreign genes, and production of foreign protein to levels of 10% of the total amount of cell protein is not unusual. Any of a variety of promoters may be used. For example, the hsp60 promoter from *M. tuberculosis* or the mycobacteriophage L5 promoter may be used.

Thus transgenic vaccines of the present invention can express many foreign antigens, unlike viral vaccine vectors that have a more limited capacity. For example, similar to efforts underway with a recombinant BCG, *M. shottsii* can be engineered to express expressing antigens, for example, from HIV, malaria, and *M. tuberculosis*, as a three-in-one vaccine. Similarly, multiple HIV antigenic sequences could be combined in a single mycobacterial-vectored vaccine—a recommended polyvalent approach to improving the breadth of HIV protection.

In comparison to viral vectors, bacterial vectors like *M. shottsii* have a large capacity for expressing inserted foreign genes. The present invention includes transgenic *M. shottsii* that express a plurality of heterologous antigens and/or immunogens.

The present invention includes vaccine compositions of native or genetically modified *M. shottsii* for use as a vaccine. Genetically modified *M. shottsii* for use as a vaccine vector is a transgenic *M. shottsii*; that is it includes one or more transgenes that function as, or encode, a foreign antigen or immunogen. Foreign antigens and/or immunogens can take the form of, for example, polynucleotides such as a DNA or RNA, as well as polypeptides. Foreign antigens or immunogens are preferably derived from a pathogenic organism, and can be, for example, viral or bacterial in origin, or obtained from a pathogenic protozoan or helminth. Optionally, the genetically modified *M. shottsii* for use as a vaccine vector includes genetic modifications that further attenuate *M. shottsii*.

A vaccine composition of the present invention may be a pharmaceutical composition, including naturally occurring or genetically modified *M. shottsii*, as well a pharmaceutically acceptable carrier. A vaccine composition may include an adjuvant. A vaccine composition may be pyrogen free. A vaccine composition may include an antiseptic agent and/or antifungal agent. A vaccine composition may include a preservative. A vaccine composition may be formulated for administration to the mucosa, for example for intranasal administration. It is expected that mucosal administration of the pharmaceutical composition to a mammalian subject will stimulate an immune response in mucosal tissues, including mucosal tissues that are remote from the site of administration, in addition to producing a systemic immune response in the subject. For example, it is expected that intranasal administration of a pharmaceutical composition of the invention will induce an immune response in genital tissue of the subject.

A vaccine composition of the present invention may be administered as a prophylactic or therapeutic vaccine or immunostimulant, and is especially suitable for administration to immunocompromised individuals.

The similarity of *M. shottsii* to *M. bovis* BCG and to other members of the MTB complex, especially in regards to its lipid coat, suggests that the vector will provide strong adjuvanticity, and induce both antibody and cell-mediated immune responses that will endure long after a single vaccine dose. Nasal vaccination is an attractive way to induce mucosal immunity, and could even be self administered in a pandemic situation.

For many reasons, *M. shottsii* has great potential as a live, attenuated vaccine against tuberculosis, which is caused by *M. tuberculosis* and which is one of the leading global causes of death. Because of its temperature-restricted growth, when administered intranasally, *M. shottsii*, will only persist in the superficial upper respiratory tissues of vaccinated mammals. The lipid composition of the cell wall of *M. shottsii* resembles that of *M. tuberculosis*. This lipid-similarity may allow *M.*

*shottsii* to induce cross-reactive and protective responses to TB through activation of group 1 CD1-restricted T cells. And, nucleic acid sequencing of several gene loci have found very high homology between *M. shottsii* genes and *M. tuberculosis* genes, raising the possibility that protein antigens may induce cross-reactive cell-mediated immunity.

BCG vaccine, which is an attenuated version of *M. bovis* developed more than 80 years ago, is routinely used to vaccinate newborns throughout most of the world because it is the only vaccine available against tuberculosis. Immunization with BCG seems most helpful in infants, reducing the incidence of severe, disseminated forms of TB. Controlled trials, however, have established that BCG offers little or no protection against the more prevalent pulmonary forms of the disease. Furthermore, BCG vaccination seems to have the least effectiveness in the regions of the world that are most ravaged by TB. In addition, BCG has made no evident impact on the global TB epidemic. The estimated number of new cases of TB and the per capita incidence worldwide continue to rise each year (A century of tuberculosis. Am J Respir Crit. Care Med. 2004; 169(10:1181-6; and Dye et al., J'AMA. 2005; 293(22):2767-753). Although the incidence of TB in the United States is no longer rising, the disease remains a significant problem in many cities, especially among immigrants and HIV-infected individuals. In the U.S., as elsewhere, the spread of multidrug resistant strains of *M. tuberculosis* threatens to effectively roll back our ability to control the disease to the situation of the pre-antibiotic era.

The best hope of bringing the global epidemic of TB under control is the development of a new, effective TB vaccine (Castanon-Arreola and Lopez-Vidal, Ann Clin Microbiol Antimicrob. 2004; 3(1):10; McMurray, Int J. Parasitol. 2003; 33(5-6):547-54; Brennan et al., Tuberculosis (Edinb). 2001; 81(5-6):365-8; and Flynn, (Edinb). 2004; 84(1-2):93-101). Because of the urgent need for a new TB vaccine, a global research effort is now underway, and a large number of living and nonliving candidate vaccines have been explored. Three candidate vaccines, a recombinant BCG over-expressing antigen (Ag) 85B, a modified vaccinia virus over-expressing Ag85A, and a fusion peptide encompassing two antigens (termed 72f) combined with an adjuvant, are now in phase I clinical trials. A transgenic *M. shottsii* of the present invention may include one of more of these antigens.

The vaccines of the present invention may be employed in many ways, for example, as preventative vaccines, as vaccines administered during latent infection to prevent reactivation, or as a therapeutic vaccine. The vaccines of the present invention may administered by any of a variety of routes. For example, they may be administered intradermally, intranasally, intramuscularly, subcutaneously, topically to a mucosal surface, or orally. In a preferred embodiment, they are administered intranasally.

*M. shottsii* vaccines of the present invention will have the advantages of a live attenuated vaccine. Live attenuated vaccines have traditionally been found to confer longer lasting immunity, and to require fewer immunizations than nonliving vaccines. These attributes make them attractive vaccine candidates for TB, which threatens people throughout their lifespans and is especially prevalent in regions of the world where lengthy immunization regimens are difficult to maintain.

Live TB vaccine candidates that have been investigated include genetically attenuated forms of *M. tuberculosis*, modified fauns of BCG, unrelated attenuated vectors such as adenovirus, vaccinia virus or *salmonella* that have been engineered to express TB antigens, and a few additional mycobacteria species (Nor and Musa, Tuberculosis (Edinb). 2004; 84(1-2):102-9; and Kamath et al., Vaccine. 2005; 23(29): 3753-61). The last category includes forms of *M. vaccae, M. microti, M. habana,* and *M. smegmatis*, several of which have demonstrated some positive results at some stage of testing, although none have undergone SCID mouse model testing to evaluate their likely safety in immunocompromised individuals.

Vaccines of the present invention overcome critical safety concerns and regulatory issues of the above discussed live TB vaccines. The greatest drawback of currently available live vaccines is the risk of causing illness or unacceptable pathology, both of which are most likely in immunocompromised people. This has become an increasingly important issue in light of the global epidemic of HIV infection. It is now well established that BCG vaccination can cause disseminated, potentially fatal, disease in immunocompromised people (Besnard et al., Pediatr Infect Dis J. 1993; 12(12):993-7; Talbot et al., Clin Infect Dis. 1997; 24(6):1139-46; Hesseling et al., Clin Infect Dis. 2003; 37(9):1226-33. Erratum in: Clin Infect Dis. 2003; 37(12):1727). (Corbett et al., Arch Intern Med. 2003; 163(9):1009-21). Because of the overlap between the HIV and TB epidemics, it is now generally agreed that any new live TB vaccine needs to be at least as attenuated, and preferably more attenuated, than the current BCG vaccine. The vaccines of the present invention provide this advantage. With the present invention, *M. shottsii* will serve as a novel platform technology for the development of vaccines for a variety of diseases. *M. shottsii* can be used either directly as a vaccine for diseases caused by other mycobacteria (such as tuberculosis), or can be genetically engineered to express inserted genes from pathogenic organisms such as HIV or influenza viruses, to create vaccines for such diseases. *M. shottsii* can be genetically engineered to express cancer genes, to create vaccines for the prevention or treatment of cancer. This highly novel and promising platform technology could form the basis of a vaccine for virtually any infectious disease for which pathogen protective antigens have been identified.

A needle-free intranasal vaccine delivery has substantial advantages over most candidate TB vaccines currently being studied. It has been clearly established that vaccination through mucosal routes, including respiratory, gastrointestinal, ocular, or urogenital mucosal surfaces, generates both mucosal and systemic immune responses, whereas systemic routes of vaccination usually only generate systemic immunity. Mucosal immunization therefore offers advantages for any pathogen that invades through or proliferates within mucosal tissues—such as *M. tuberculosis*. The ability of mucosal vaccination to also induce systemic immunity means that vaccine efficacy can also encompass host defense against disseminated bacilli. The fact that mucosal immunization does not require needles and syringes can be a highly desirable attribute in some situations. The present invention can be used to deliver vaccines to mucosal surfaces and to deliver vaccines without the use of needles Of the various mucosal routes of vaccination, intranasal vaccination has attracted the most attention, both because of the ease of administration and because of many demonstrations of intranasal vaccine efficacy (Kyd et al., Vaccine. 2001; 19(17-19):2527-33; Davis, Adv Drug Deliv Rev. 2001; 51(1-3):21-42; Illum and Davis, Adv Drug Deliv Rev. 2001; 51(1-3):1-3; and Kyd et al., Vaccine. 2001; 19(17-19):2527-33). Many intranasal vaccines for veterinary applications are already on the market. To date, the only human intranasal vaccine in clinical use (at least in the U.S.) is FluMist® intranasal flu vaccine, but intranasal vaccines for other human diseases are in various stages of development, including vaccines incorporating malarial, schistosomal, or HIV antigens as intranasal vaccines against those diseases.

In light of the advantages of intranasal vaccination, it is surprising that so little of the global research on TB vaccination strategies has been directed towards exploiting this route of immunization. Three prominent TB vaccine development groups—a group at McMaster University, Adrian Hill's group at Oxford, and Juraj Ivanyi's group at Kings College London—have published efficacy studies on intranasally administered BCG (Falero-Diaz et al., Vaccine. 2000; 18(28): 3223-9; Chen et al., Infect Immun. 2004; 72(1):238-46; Goonetilleke et al., J. Immunol. 2003; 171(3):1602-9). Several investigators have also published efficacy studies using attenuated strains of vaccinia virus and adenovirus, each genetically engineered to express TB antigen 85A (Goonetilleke et al., J. Immunol. 2003; 171(3):1602-9; and Wang et al., J. Immunol. 2004; 173(10):6357-65). Intranasal vaccination with each of these vectors has demonstrated potent induction of pulmonary immune responses in addition to systemic immunity, and protective efficacy against subsequent aerosol challenge with virulent *M. tuberculosis*.

Studies utilizing each of these live attenuated organisms have confirmed that intranasal vaccination is a highly promising approach to inducing protection against TB, and have additionally elucidated some of the mechanisms of immunity induced. These include recruitment, prolonged retention, and functional activation of pulmonary T cells (Chen et al., Infect Immun. 2004; 72(1):238-46; Goonetilleke et al., J. Immunol. 2003; 171(3):1602-9; Wang et al., J. Immunol. 2004; 173 (10):6357-65; Copenhaver et al., Infect Immun. 2004; 72(12):7084-95; Dieli et al., J. Immunol. 2003; 170(1):463-9; Santosuosso et al., J. Immunol. 2005; 174(12):7986-94; and Lyadova et al., Clin Exp Immunol. 2001; 126(2):274-9), induction of delayed-type hypersensitivity (DTH) to the TB skin test reagent PPD (Nuermberger et al., Infect Immun. 2004; 72(2):1065-71), enhancement of the ability of alveolar macrophages to kill intracellular *M. tuberculosis* (Drandarska et al., hit Immunophannacol. 2005; 5(4):795-803), and recruitment of dendritic cells to the lungs (Reljic et al., Tuberculosis (Edinb). 2005; 85(1-2):81-8; Lagranderie et al., Immunology. 2003; 108(3):352-64), where they direct polarization of T cells towards the Th1 phenotype (Lagranderie et al., Immunology. 2003; 108(3):352-64). Thus a growing body of evidence indicates that intranasal vaccination with live attenuated organisms is a promising approach to vaccination against tuberculosis. In the larger context of research on possible TB vaccines, however, it is appropriate to say that our studies will be among a relatively few that have involved intranasal immunization with a candidate TB vaccine. Even fewer studies have directly compared the same vaccine preparation given either intranasally or by a systemic route. Our studies, therefore, will advance scientific understanding in an important area of research, as well as possibly leading to a needle-free TB vaccine.

The HPLC lipid analysis "signature" of *M. tuberculosis* is a single cluster of eight mycolic acid peaks (Butler and Guthertz, Clin Microbiol Rev. 2001; 14(4):704-26). The *M. shottsii* chromatogram has a similar set of eight mycolic acid peaks that elute slightly faster than those of *M. tuberculosis*, indicating that the mycolic acids are slightly shorter and more polar than those of *M. tuberculosis* (Rhodes et al., Emerg Infect Dis. 2001; 7(5):896-9). Although the precise molecular requirements for lipid antigen presentation through the group 1 CD1 pathway are still being elucidated, it is believed that lipid antigen presentation is more flexible (less constrained) than peptide epitope presentation. For example, the CD1B antigen binding groove consists of four "pockets". The length of the alkyl chain of a lipid antigen determines how many pockets in the antigen binding groove are occupied by the lipid antigen, but lipids of varying chain lengths are effectively presented by CD molecules (Brigl and Brenner, Annu Rev Immunol. 2004; 22:817-90). Therefore it is very reasonable to expect that the slight differences between the lipids of *M. shottsii* and those of *M. tuberculosis* would be inconsequential in terms of antigen presentation.

The vaccines of the present invention may be administered intranasally. Most people prefer administration as a nasal spray over injection by a needle, both for themselves and for their children. Additionally, the WHO has set the development of "needle-less" vaccines as a global public health goal, because of the risk of inadvertently spreading blood-borne diseases through the misuse of needles. Furthermore, intranasal vaccination induces mucosal immunity as well as systemic immunity, whereas injections only induce systemic immunity. Since almost all pathogens infect the body through mucosal surfaces, the respiratory tract, the gut, or genital tissues, mucosally administered vaccines have more opportunity to stop infectious diseases at the point of entry.

The vaccines of the present invention have the advantages of live vaccines, yet will be very safe because of their inability to survive at mammalian core body temperatures. Of the various forms of vaccines, usually classified as live whole cell, dead whole cell, subunit, or DNA-based, it is well recognized that live whole cell vaccines induce the most durable protection.

The vaccines of the present invention are expected to induce T-cell-mediated immunity as well as antibodies. This ability to induce both types of immunity is a feature of immune responses to mycobacteria in general. Almost all vaccines in the marketplace today only induce antibodies, but there are many infectious diseases caused by pathogens that can only be eliminated from the body by T-cell-mediated immunity.

Although cold-adapted viruses may seem similar to the naturally cold-adapted *M. shottsii* vaccine platform of the present invention, the present invention has advantages. For example, the genome of *M. shottsii* is immensely larger than those of a virus (thousands of genes versus just a few genes). When viruses are used as vectors to present antigens from other pathogens to the immune system, only one or two foreign genes can be packaged into the viral shell. In contrast, numerous foreign genes can be inserted into *M. shottsii*. For example, one could create an *M. shottsii*-based vaccine to protect against every known human sexually-transmitted disease. Or, a vaccine containing antigens from the agents of tuberculosis, malaria, and HIV may be constructed in *M. shottsii*.

The present invention is illustrated by the following examples. It is to be understood that the particular examples, materials, amounts, and procedures are to be interpreted broadly in accordance with the scope and spirit of the invention as set forth herein.

EXAMPLES

Example 1

*Mycobacterium shottsii*, as a Vaccine for Tuberculosis

This example will assess the potential of *M. shottsii* as a vaccine for tuberculosis (TB). It includes three Aims. Aim One is an evaluation of safety by comparing *M. shottsii* to BCG in severely immunodeficient SCID mice. SCID mice are a model system that is increasingly being accepted by TB vaccine developers and regulatory authorities as a verification of attenuation that may predict the safety of a live vaccine in immunocompromised human subjects. It is expected that *M. shottsii* will be equally or more attenuated than BCG in the SCID mouse model.

Aim Two includes additional studies of vaccine safety and immunogenicity, performed in immunocompetent, outbred Hartley strain guinea pigs. The experiments will compare graded doses of *M. shottsii* to graded doses of BCG bacilli (a live attenuated vaccine derived from *M. bovis*), either applied by the intranasal route of administration or delivered as an intradermal injection. Guinea pigs will be vaccinated, but not challenged. Three important aspects of evaluating the safety of *M. shottsii* as a live vaccine will be evaluated. One, pathogenicity and vaccine reactogenicity will be assessed by clinical measurements, and by postmortem histological studies of tissues both at the site of inoculation and in potential sites of dissemination such as the lungs and spleen. Two, microbial persistence, both locally and at potential sites of dissemination, will be ascertained by culture of recoverable organisms. And, three, possible "reversion to virulence" (or as more accurately stated for a naturally attenuated strain like *M. shottsii*—in vivo acquisition of increased virulence) over a period of time in a mammalian host will be assessed by determining if recovered *M. shottsii* bacilli have become any more thermotolerant than the original inoculum.

Aim Three includes vaccine efficacy studies utilizing the well established guinea pig model of TB. Guinea pigs (*M. shottsii* vaccinated, BCG vaccinated, and unvaccinated) will be observation for up to 300 days following inoculation. Animals will be sacrificed for cultures and pathology studies at 300 days post-inoculation and sooner if any of the guinea pigs display signs of illness.

The temperature sensitivity of *M. shottsii* will keep it confined to the superficial tissues of the upper respiratory passages, just as is true for cold-adapted influenza strains. To test this, the studies under Aims One and Two will not only carefully test for evidence that *M. shottsii* may have disseminated to warner tissues, but will also test both nasal and other tissues for evidence of bacilli that may have adapted in vivo for any less temperature restriction than was characteristic of the initial inoculum.

Experimental Design and Methods

Virulent *M. tuberculosis* used for challenge will be H37Rv, maintained in the laboratory. Fresh cultures of the H37Rv type strain may be obtained from the ATCC. The BCG vaccine comparator strain will be BCG Pasteur.

Fresh clones of *M. shottsii* will be isolated from Chesapeake Bay striped bass, taking care to employ only certified BSE-free materials. A Master Seed Bank and a Working Seed Bank will be established. This is the standard, FDA recommended, procedure for preventing genetic variations from creeping into a vaccine strain. All work with the *M. shottsii* vaccine strain will be conducted under Good Laboratory Practice (GLP) guidelines. The temperature growth restriction will be determined for the vaccine isolate. All of the components needed to establish a Master and Working Seed banks are commercially available with the "BSE-free" designation. Isolates of will be verified by species-specific PCR testing and HPLC lipid analysis.

Aim One

The evaluation of the safety of *M. shottsii* will be a comparison of *M. shottsii* to BCG in highly immunodeficient SCID mice. SCID mice, which lack both T cells and B cells, have proven to be a useful and sensitive model for comparing the virulence of different mycobacterial strains or species (Sambandamurthy et al., Nat. Med. 2002; 8(10):1171-4). Important evidence in support of the feasibility of proceeding with further assessment of the vaccine potential of *M. shottsii* will be a finding that *M. shottsii* is no more virulent than BCG in the SCID mouse. Furthermore, postmortem studies will allow a comparison of tissue pathogenicity caused by *M. shottsii* to that caused by BCG, comparative persistence of the two mycobacterial species, and, if any viable *M. shottsii* are recovered, the possibility that during persistence in a mammalian host, *M. shottsii* might have become less temperature-restricted in its growth than was the original vaccine strain.

Published protocols that were used in demonstrating the attenuation of the double auxotrophic mutant of *M. tuberculosis* in SCID mice (Sampson et al., Infect Immun. 2004; 72(5):3031-7) will be used. Three groups of eight JAX® B6.CB17-Prkdc SCID mice will be intravenously injected with either PBS (control) or $3\times10^4$ log-phase bacilli of either BCG or *M. shottsii*. The read-out of this assay is termed survival time, but the mice will be monitored for signs of illness, and will be euthanized as directed by veterinary staff blinded to the treatment groups. It is expected that the BCG injected mice will succumb between 8 and 11 weeks after inoculation. The expected survival time of SCID mice injected with *M. shottsii* is unknown. As BCG and *M. shottsii* injected mice succumb or are euthanized for declining health tissues from the lungs, liver, spleens, and nasal passages of the mice will be examined for gross pathology and micropathology if warranted and cultured for growth of persisting mycobacteria, both on agar plates and in broth (which is not quantitative, but is considered to be more sensitive if the number of inoculated mycobacteria is low). For BCG, the incubation temperature will be 37°; for *M. shottsii* incubation at 23°, 26°, 29° and 37° will probe for any change in temperature growth restriction compared to the vaccine innoculum.

Data analysis and interpretation. Group sizes are powered for comparison of survival curves, which will be compared using the logrank test (Bland and Altman, "Statistics Notes: The logrank test," BMJ May 1, 2004; Vol. 328 at bmj.com; and Bland and Altman, "Statistics Notes: Survival probabilities (the Kaplan-Meier method)," BMJ 1998; 317: 1572-1580 at bmj.com). The first logrank analysis will be conducted when the BCG injected mice have succumbed, and will be used to test the null hypothesis that there is no difference between the survival curves of the BCG and *M. shottsii* injected mice. Note that the logrank test, like the Kaplan-Meier method, is appropriate to use when some individuals have not yet died (in statistical terms, some survival times are censored). No significant difference between the BCG and *M. shottsii* survival curves means that *M. shottsii* is as attenuated as BCG in this model. If the *M. shottsii* injected mice survive longer than the BCG injected mice, and the survival curves are clearly different for this reason, this will mean that *M. shottsii* is more attenuated than BCG in this model. *M. shottsii* and PBS injected groups will be followed for as long as the *M. shottsii* injected mice survive, up to a maximum of 270 days post-injection. A final statistical analysis of all three groups, using the logrank test, will be performed. If the survival curve of the *M. shottsii* mice is not statistically different from the PBS control group, this will mean that the *M. shottsii* vaccine is avirulent in a severely immunodeficient mouse model that is increasingly being accepted as predictive of safety in immunocompromised people.

Tissue pathology will not be quantified, but any evidence of tissue pathology that was markedly greater in the *M. shottsii* injected SCID mice than in the BCG injected mice would be noted. Numbers of recovered CFU from the organs of mice in the BCG and *M. shottsii* groups will be compared by the Student t test.

Survival curves of the three groups of SCID mice will be compared. An expected finding is that *M. shottsii* is as attenuated as, or more attenuated than, BCG in this animal model.

Aim Two

Additional studies of vaccine safety and immunogenicity will be performed in immunocompetent outbred Hartley strain guinea pigs. These studies are designed, in part, in consideration of recent statements by regulatory officials and knowledgeable vaccine developers concerning the preclinical animal studies that are desirable or necessary before a live TB vaccine candidate would be approved for entry into human trials. The objectives include:

Assess tissue pathology, including that due to the immune response induced by a vaccine;

Assess microbial persistence in an immunocompetent animal model;

Determine whether *M. shottsii* organisms that may be recovered after a period of in vivo persistence may have adapted by becoming less temperature-restricted in their growth;

Assess whether *M. shottsii* vaccination would induce cutaneous DTH responses to PPD (Although there could be a small public health disadvantage if vaccination with *M. shottsii* were found to cause positive PPD skin tests in vaccinated people, this is not considered to be an obstacle for an effective TB vaccine. BCG vaccination causes positive PPD responses that persist for decades. Dose-related positive PPD reactions in the guinea pigs could form the basis of a potency test that is a requirement for sound product development. For, example, induction of PPD reactions in guinea pigs is the potency test for manufacture of BCG vaccines); and Attempt to identify a measure of immunogenicity by quantifying guinea pig antibodies to native TB proteins in the antigen 85 complex, with the objective being development of a potency test.

Experimental groups. Four Charles River Laboratory Hartley strain guinea pigs, weighing 201-250 grams each, randomized into each of eights groups will be immunized as outlined in Table 1. A ninth group will be unimmunized, and will serve as a healthy control group.

TABLE 1

| | Intranasal Inoculum | | Intradermal Inoculum | |
|---|---|---|---|---|
| *M. shottsii* | $10^5$ | $10^6$ | $10^5$ | $10^6$ |
| BCG | $10^5$ | $10^6$ | $10^5$ | $10^6$ |

Intranasal administration. BCG or *M. shottsii* will be administered to the guinea pigs as drops. The volume of liquid vaccine administered may be critical in determining the distribution of the liquid along the respiratory and gastrointestinal tracts (Pasetti et al., J. Virol. 2003; 77(9):5209-17). It has been determined that the nasal spray administration of FluMist results in distribution of the vaccine droplets in the nasopharynx (Abramson, Pediatr Infect Dis J. 1999; 18(12): 1103-4; and Cox et al., Scand J. Immunol. 2004; 59(1):1-15). As anyone who has used a nasal spay has noticed, any excess spray that trickles down the throat of awake humans is swallowed. In anesthetized animals, intranasally administered liquid can drain into the lungs as well as into the gastrointestinal tract. Straszek and Pedersen measured nasal cavity dimensions in guinea pigs, and estimated that the volume of the nasal cavity in guinea pigs is the equivalent of 100 to 200 microliters per side (Straszek and Pedersen, J Appl Physiol. 2004; 96(6):2109-14). Intranasal vaccines will be administered to lightly anesthetized guinea pigs in a volume of 25 microliters per side, applied just inside the external nares while the guinea pigs are in a dorsal recumbent position (for no more than 5 minutes), in order to optimize the retention of the vaccine in the nasopharynx as would be characteristic of a vaccine administered to humans by a device such as that used for FluMist®.

Intradermal administration. Guinea pigs in the Aim Two studies will be vaccinated by a systemic route, for comparison to vaccination by the intranasal route, and to lay the groundwork for selection of a prime-boost protocol in the vaccine efficacy studies in Aim Three. Intramuscular, intraperitoneal, subcutaneous, and intradermal vaccinations are all systemic routes of immunization. An intradermal route of vaccination will be used for several reasons.

The WHO recommends that BCG vaccination be given intradermally, and most countries administer BCG by this route. Interestingly, a recent comparative trial has found that intradermal BCG vaccination (with a needle) is more effective than percutaneous vaccination (with a specialized vaccine applicator involving multiple tines) (Hussey et al., Immunology. 2002; 105(3):314-24). The reason for the difference in efficacy may have to do with the differences in the dendritic cells that take up the antigens. In the epidermis, where intradermal vaccination is supposed to deliver the antigens, Langerhans cells are the resident dendritic cells. Slightly deeper in the skin, in the dermis, the resident dendritic cells are interstitial dendritic cells (Liu, Cell. 2001; 106:259-262). Percutaneous vaccination with the tine device probably deposits some of the antigens into this layer of the skin. Exciting studies of the lipid antigen presenting capacity of Langerhans cells have informed the decision to use intradermal vaccination in the Aim Two studies. The specific isoforms of group 1 CD1 antigen presenting molecules appear to be different on Langerhans cells than on interstitial dendritic cells (Moody and Porcelli, Nat Rev Immunol. 2003; 3(1):11-22). Furthermore, two recent studies have shown that epidermal Langerhans cells efficiently present mycobacterial lipids to T cells (Hunger et al., J Clin Invest. 2004; 113(5): 701-8; and Pena-Cruz et al., J Invest Dermatol. 2003; 121(3): 517-21).

Clinical observations and scoring. All guinea pigs, regardless of the route by which they are vaccinated, will be monitored daily during the first week for increased body temperature or evident malaise. All guinea pigs will be weighed weekly to detect anorexia or other adverse reactions that can affect weight. Intradermally injected guinea pigs will have their injection sites visually inspected, at first daily and then weekly. A scoring system for monitoring upper respiratory vaccine reactogenicity will be used to derive a quantitative score for each intranasally vaccinated guinea pig. The elements of the scoring system will be: visible inflammation of the external nares (0-3); nasal discharge characterized as none, slight serous, marked serous, slight mucopurulent, or marked mucopurulent (0-4) (Patel, J S Aft Vet Assoc. 2004; 75(3):137-46); and respiratory rate, which has been validated as an index that reflects nasal blockage of guinea pigs (0-3) (Zhao et al., Rhinology. 2005; 43(1):47-54).

Measures of immunogenicity will include measurements of cutaneous DTH to PPD and antibody responses to antigen 85 complex. For measurments of cutaneous DTH to PPD, all guinea pigs will be given an intradermal injection of PPD 39 days after vaccination (i.e. three days before the six week sacrifice point) using a standardized protocol (Sampson et al., Infect Immmun. 2004; 72(5):3031-7) and induration at the site will be measured 24, 48, and 72 hours later. The 39 day time point may be a little too soon for a cutaneous DTH reaction to develop. Thus, the study is designed with three out of four animals in each experimental group being sacrificed at six weeks largely to increase our chances of recovering persistant mycobacteria before an increasing cell-mediated immune response might eliminate the organisms. The one remaining guinea pig in each experimental group can be retested at nine weeks post-inoculation, as an attempt to overcome this pitfall, but each intradermal injection of PPD will boost immunity to the antigens in PPD, and thus may alter immune-mediated pathology.

Antibody responses to the antigen 85 complex (85A, 85B, and 85C) will be measured six weeks after vaccination, three animals in each experimental group will be euthanized for pathology and microbiology studies, and at that time blood will be drawn by cardiac puncture. Serum will be banked for further studies in Phase II, and a portion will be tested in an ELISA for antibodies to proteins of the antigen 85 complex. Native (i.e. not recombinant) antigen 85 complex protein mixture will be obtained from the NIAID-sponsored TB Resources program at Colorado State University. The antigen 85 complex is believed to be encoded by highly homologous genes in all mycobacterial species, so this is a reasonable choice of an immunogenicity measure that could be used as a potency assay. Measurement of interferon-gamma producing ELISPOTS by mice immunized with the Oxford group's MVA85A vaccine is used as their vaccine potency test. Note that potency assays vary by product and may evolve as a product moves through preclinical and clinical studies (NIH/FDA TB Vaccine Workshop). Also, note especially that neither of our measures of immunogenicity are thought to be correlates of vaccine protection.

Postmortem studies. Three guinea pigs in each experimental group will be sacrificed six weeks after vaccination, while one animal in each group will be maintained for 270 days for evidence of late reactivation of disease, longer term persistence, and testing of the temperature restriction of any persisting *M. shottsii* that are recovered.

After euthanasia, tissues including lungs, liver, spleens, nasal tissues and punch biopsies of intradermal injection sites will be harvested and allocated to different experiments. Gross pathology and microhistopathology studies will be conducted by a veterinary pathologist using methods and a scoring system that have been developed specifically for determination of mycobacteria-related pathology (Lasco et al., Tuberculosis (Edinb). 2005; 85(4):245-58). These methods will also be applied to the virulent TB challenged guinea pigs in Aim Three, as described below.

Microbiological studies will include culture of tissue homogenates for CFUs, including culture of homogenates from *M. shottsii* vaccinated mice at incubation temperatures of 23°, 26°, 29°, and 37° C., to assess any loss of temperature restriction. If some persistence of *M. shottsii* is found in the nasal tissues of mice, but not elsewhere, this will confirm that the natural cold-adaptation of *M. shottsii* will keep it confined to the upper respiratory tract, just as is true for cold-adapted live flu vaccine. Furthermore, some persistence of a live vaccine is a good thing, as it helps in inducing a strong and durable immune response.

Data analysis and interpretation. CFUs are, of course, quantitative, as are induration sizes of PPD reactions and ELISA optical density measures. A scoring system will be used for clinical observations and pathology studies to yield a quantitative measurement. Each of these measures will be compared by the Student t test for significant differences between groups.

Aim Three

Preliminary efficacy studies comparing *M. shottsii* to BCG in guinea pig model of TB. Aim Three will demonstrate that vaccination with *M. shottsii* has efficacy in the guinea pig model of TB. Based upon the results of the Aim Two, a single inoculum dose will be selected for intranasal immunization and a single dose for intradermal immunization. Guinea pigs will be aerosol challenged with virulent *M. tuberculosis* seven weeks after vaccination (or after the last vaccination in the case of the prime-boost regimens in trial two, described below. Experimental group sizes of five animals per group are based upon Mary Hondalus' recently published studies in which that group size yielded statistically significant differences between vaccinated and control guinea pigs for the outcome measure of CFUs of the *M. tuberculosis* challenge strain, which will also be our primary outcome measure. Two efficacy trials will be conducted sequentially, mainly because of the capacity limit of the Madison aerosol exposure chamber, but also so that we can factor the results of the first trial into the design of the second trial.

The first trial will compare the protective efficacy of intradermally administered BCG, intradermally administered *M. shottsii*, intranasally administered BCG, intranasally administered *M. shottsii*, and unvaccinated controls. One additional unvaccinated animal will be sacrificed shortly after the aerosol exposure to confirm that approximately 20 CFUs of *M. tuberculosis* H37Rv were deposited into the lungs during the aerosol exposure.

The second trial will compare four prime-boost regimens, with eight weeks elapsing between the prime and the boost. Groups of ten guinea pigs will be intradermally vaccinated with either BCG or *M. shottsii*, and then divided into groups of five, which will be boosted intranasally with either BCG or *M. shottsii*. This trial design has been selected, in part, because it models one way that a new TB vaccine may be used. As recently published, in a report of a successful prime-boost regimen in the guinea pig TB model, one approach to improving resistance to TB is to use a new vaccine to boost immunity in children who have already been vaccinated at birth with BCG (Horwitz et al., Infect Immun. 2005; 73(8): 4676-83). The great majority of children (and a majority of adults) living in the areas of the world with high TB prevalent are vaccinated at birth with BCG as per WHO recommendations, and it may be difficult to even conduct Phase 3 clinical trials of a new vaccine if participation requires withholding BCG vaccination.

Guinea pigs will be sacrificed five weeks after challenge. CFU of *M. tuberculosis* will be cultured by standard methods. Pathology will be interpreted by a veterinary pathologist and scored by a system developed specifically for the guinea pig model of TB (Lasco et al., Tuberculosis (Edinb). 2005; 85(4): 245-58). Guinea pigs will be weighed weekly.

Data analysis and interpretation: The Aim Three studies are powered for comparison of log CFU in the lungs and spleens of vaccinated groups to the non-vaccinated (control) group, determined by one-way analysis of variance. It is expected that at least some vaccine regimens show that *M. shottsii* has statistically significant vaccine efficacy, as compared to the control group. It is very unlikely that we could find statistically significant superiority of *M. shottsii* over BCG in these trials, because demonstrating superiority over BCG of the very best candidate vaccines tested in the guinea pig model has required group sizes on the order of 24 guinea pigs per group. ANOVA methods will also be used to compare mean weight gains/losses.

Example 2

Toxicity and Immune-Reactivity of *M. shottsii* via Intranasal Infection

This example demonstrates that intranasal inoculation with a large dose of *M. shottsii* produces minimal toxicity in the nasal cavities (similar to or less than *M. bovis* BCG) and none in the lungs or other examined organs (less than *M. bovis* BCG). Of equal or greater importance is the observed ability by *M. shottsii* to induce a similar immune response in the NALT as compared to that of *M. bovis* BCG. Further studies will examine humoral and cellular immune responses in the guinea pig and will demonstrate as good as or superior to *M. bovis* BCG with less toxicity.

Detailed histopathology studies were conducted, examining the nasal associated lymphoid tissue (NALT) and the lungs of mice that were intranasally vaccinated with either $10^7$ *M. shottsii* or $10^7$ BCG organisms. In order to assess the toxicity and initial immune-reactivity of *M. shottsii* via intranasal infection, three groups of five C57BL/6 mice were inoculated with PBS, $10^7$ CFU *M. bovis* BCG, strain Pasteur or $10^7$ *M. shottsii* and were assessed 7- and 21-days post-challenge. At necropsy, gross examination of mouse carcasses found no significant lesions in nasal cavities, trachea, lungs and other organs in all groups of mice at the 7 and 21 days post-infection time points. Whole head and lungs were dissected out from the body and placed in 10% buffered formalin for overnight fixation. Mice heads were then decalcified overnight and serially sectioned between the 3rd and 4th palatine ridges to expose the Nasal Associated Lymphoid Tissues (NALT). Serial sections were placed in tissue cassettes and stained with hematoxylin and eosin stain (H&E).

Representative histological appearance of NALT from C57BL/6 mice after 21-day infection by intranasal challenge with PBS control, $10^7$ CFU of *M. bovis* BCG, or *M. shottsi* showed moderate expansion of lymphoid follicles of NALT is seen in BCG and *M. shottsii*-infected mice. NALT in these inoculated groups display increased numbers of lymphoblasts and macrophages indicating immune-reactivity to the given antigen. In some sections, there is increased density of lymphatics/capillaries within hyperplastic lymphoid follicles. Comparatively, there is no expansion of NALT in control group of mice. Lymphoid follicles within control group have relatively higher numbers of small lymphocytes interspersed with fewer macrophages and lymphoblasts.

Histologically, there is a gradual expansion of lymphoid follicles in the NALT from 7- to 21-day post-infection in mice inoculated with *M. bovis* BCG and *M. shottsii*. Additionally, the NALT in both inoculated groups display increased numbers of lymphoblasts and macrophages indicating immune-reactivity against mycobacterial antigens. In some sections, there is increased density of lymphatics/capillaries within hyperplastic lymphoid follicles. Comparatively, there is no expansion of NALT in control groups of mice at either time point. Lymphoid follicles within the control group have relatively higher numbers of small lymphocytes interspersed with fewer macrophages and lymphoblasts. The lung tissues from the three groups of mice sacrificed at both time points showed no grossly visible lesions. Lung tissues from *M. bovis* BCG inoculated mice after 21-day infections showed microscopic granulomas, often located in sub-pleural areas. Lungs of mice inoculated with *M. shottsii* or sterile PBS at the same time point showed no evidence of granulomas in the parenchyma.

These studies indicate that intranasal inoculation with a large dose of *M. shottsii* produces minimal toxicity in the nasal cavities (similar to or less than *M. bovis* BCG) and none in the lungs or other examined organs (less than *M. bovis* BCG). Of equal or greater importance is the observed ability by *M. shottsii* to induce a similar immune response in the NALT as compared to that of *M. bovis* BCG.

Example 3

Expression of a Heterologous Protein in *M. shottsii*

The green fluorescent protein (GFP) from the jellyfish *Aequorea victoria* is a frequently used reporter protein for monitoring gene expression and protein localization in a variety of cells and organisms. See for example, the review by R. Tsien, Ann. Rev. Biochem 1998; 67:509-544.

Using a mycobacteriophage L5 promoter to drive expression of the gene for green fluorescent protein (GFP), *M. shottsii* has been genetically engineered to express GFP. GFP-expressing *M. shottsii* were used to infect a carp macrophage cell line (ATCC-CCL30), in which the mycobacteria can be observed to be intracellular. This suggests that *M. shottsii*, like other mycobacteria of the *M. tuberculosis* complex, is a facultative intracellular microbe. If *M. shottsii* bacilli also persist or grow intracellularly in mammalian cells, this characteristic would bode well for the ability of an *M. shottsii* vaccine to induce Th1 immunity, which is believed to be important for an effective immune response to *M. tuberculosis*. The intracellular growth of *M. shottsii* in mammalian cells is difficult to investigate, because *M. shottsii* will not grow at 37° C., and mammalian cells will not generally grow at cooler temperatures. Future studies will explore the ability of human nasopharyngeal epithelial cells to grow at a temperature that would be permissive for *M. shottsii*, and these studies will be of great interest to us because of their relevance to the use of *M. shottsii* as an intranasal vaccine.

Example 4

Immune Response in Animals Immunized with *M. shottsii* Expressing a Transgene

To determine the induction of an immune response to an antigen or immunogen provided by immunization with a transgenic *M. shottsii* vector, groups of BALB/c mice will be vaccinated intranasally with either:
  saline only, as a negative control group;
  one dose ($10^7$ organisms) of GFP-expressing *M. shottsii*;
  two doses of GFP-*M. shottsii*, two weeks apart; or
  three doses of GFP-*M. shottsii*, at two week intervals.
Three weeks after the last vaccination, the mice will be humanely sacrificed and their serum collected for detection of antibodies.

By Western blot analysis, mixtures of proteins will be separated by electrophoresis on polyacrylamide gels. Gels will contain either a sonicate of the *M. shottsii* expressing GFP or purified GFP alone. Proteins from the gels will be transferred onto nitrocellulose, incubated with serum from each mouse. Bound antibodies will be detected with enzyme-labeled secondary antibodies.

Example 5

*Mycobacterium shottsii* Based HIV Vaccines

This example will develop *M. shottsii* as a transgenic vaccine vector. *M. shottsii* is a member of the *Mycobacterium*

*tuberculosis* complex, a phylogenetic grouping of genetically similar mycobacterial species that includes *M. tuberculosis*, *M. bovis*, and the live vaccine BCG, which is an attenuated strain of *M. bovis*. Recombinant BCG vaccines expressing various HIV antigens have shown promising results in small animal and nonhuman primate models, producing strong HIV antigen-specific T cell responses, neutralizing antibody responses, and exceptionally durable immunity.

While BCG is a powerful vaccine vector, it has become increasingly evident that BCG vaccination of immunocompromised individuals can result in disseminated BCG infections and fatal disease. Thus safety concerns may make BCG-HIV vaccines impractical, especially in settings where it may not be feasible to identify and withhold vaccine from all immunocompromised individuals. Furthermore, BCG vaccine bacilli persist in vaccinated human subjects for years, even decades, and there are documented examples of disseminated BCG disease developing long after vaccination, when an individual's immune system became compromised.

Example 3 will show that *M. shottsii*, like BCG, can be genetically engineered to express foreign genes and, thus, serve as a vaccine vector. Safety issues of BCG-based HIV vaccines can be overcome by exploiting a unique property of *M. shottsii*. Although phylogenetically closely related to BCG, *M. shottsii* differs from all other members of the *Mycobacterium tuberculosis* complex in one dramatic way. *M. shottsii* is naturally cold-adapted, growing best at around 22-26° C., and not at all at 37° C., allowing it to replicate and persist only in the superficial upper respiratory tissues of vaccinated mammals.

In this example, HIV gag p24 protein expression will be optimized from mycobacterial promoters and secretion signals in *M. shottsii*. *M. shottsii* will be engineered to abundantly express HIV proteins that have been codon-optimized for expression in mycobacteria. This example will compare the relative safety of *M. shottsii* to the live BCG vaccine administered intranasally to immunocompromised (SCID) mice. The natural temperature-sensitivity of *M. shottsii* will restrict replication to the upper respiratory tissues and it will not persist or grow in the deeper tissues as BCG does. This example will also determine the immunogenicity of selected *M. shottsii* gag p24-expressing strains. Intranasal vaccination will induce p24 antigen-specific antibodies and cell-mediated immune responses both systemically and in distant mucosal tissues of the genital and intestinal tracts.

A vaccine to prevent HIV infection and disease offers the best hope of bringing the worldwide HIV epidemic under control. The most essential features of an HIV vaccine are that it be effective, safe, and inexpensive. Based upon the discussion below, *M. shottsii* vectored HIV vaccine will fulfill these criteria. While the correlates of protection for an HIV preventative vaccine are not yet fully elucidated, at least three points are likely to hold true. One, both cell-mediated immunity and neutralizing antibodies are likely to contribute to host defense. Two, the great majority of HIV infections are acquired by the vaginal or rectal routes, a preventative vaccine should induce effective immunity in these mucosal sites as well as systemically. And, three, immunity must be induced to multiple epitopes, and preferably to multiple antigens, to protect against the many strains of HIV and to reduce the risk that a strain can escape immunity by acquiring mutations in key epitopes.

Live attenuated vaccines have traditionally been found to confer longer lasting immunity, and to require fewer immunizations than nonliving vaccines. These attributes make them attractive vaccine candidates for HIV, which threatens people throughout their life spans and is especially prevalent in regions of the world where lengthy immunization regimens are difficult to maintain. Among the live vaccine vectors that have been considered as delivery vehicles for HIV antigens, BCG was proposed as a promising candidate early on, because of several attractive features. Among the most promising features of BCG are its ability to be engineered to express very high levels of foreign proteins, its intrinsic powerful adjuvanticity, its ability to induce cell-mediated immunity that is biased towards Th1, its ability to be administered mucosally and to induce mucosal immunity, its 80 year history of use as a human vaccine, and the fact that it can be manufactured very inexpensively.

A wide variety of systems for the introduction and expression of foreign genes in BCG and other mycobacteria have been developed. Two general classes of vectors exist—shuttle plasmid vectors that replicate extrachromosomally and that can carry 20 kb or more of foreign genetic material, and shuttle phasmid vectors that stably integrate into the mycobacterial chromosome along with much larger amounts of foreign DNA. Thus mycobacterial vaccines can express many foreign antigens, unlike viral vaccine vectors that have a more limited capacity. For example, nonhuman primate trials are now underway with a recombinant BCG expressing antigens from HIV, malaria, and *M. tuberculosis*, which is designed to be a three-in-one vaccine. Similarly, multiple HIV antigenic sequences could be combined in a single mycobacterial-vectored vaccine—a recommended polyvalent approach to improving the breadth of HIV protection. By selecting various leader sequences or even by inserting foreign DNA into the sequence of a mycobacterial gene, it is possible to direct the expressed protein to the cell membrane, or to remain in the cytoplasm, or to be exported from the cell. Furthermore, a large number of native or foreign promoters are available to drive the expression of foreign genes, and production of foreign protein to levels of 10% of the total amount of cell protein is not unusual. Use of a strong promoter, choice of leader sequences, and codon optimization have been shown to act synergistically to increase HIV vaccine immunogenicity.

The adjuvanticity of BCG and other mycobacteria in the *Mycobacterium tuberculosis* complex can largely be attributed to components of the mycobacterial cell wall, and especially to trehalose dimycolate, also known as cord factor. Cell wall fractions of *M. tuberculosis* are the key ingredient that provides the immune stimulating property of Complete Freunds Adjuvant. A major glycolipid component of the cell wall of all pathogenic mycobacteria is trehalose dimycolate, which has been shown to activate innate immune mechanisms believed to account for adjuvanticity. Synthetic analogs of trehalose dimycolate form the basis of the adjuvant Titer-Max®. The cell wall lipid profile of *M. shottsii* is extraordinarily similar to that of *M. tuberculosis* (and to a slightly lesser extent to BCG). Further, based on the way it grows in culture, it is likely that *M. shottsii* produces trehalose dimycolate. Trehalose dimycolate is called cord factor because mycobacteria that produce it tend to bind together in long, winding, rope-like structures. These same characteristic structures have been observed in cultures of *M. shottsii*. It is reasonable to expect, therefore, that *M. shottsii* is likely to have the same powerful adjuvant properties as BCG—inducing strong Th1 T cell responses, along with moderate Th2 and antibody responses, and activating innate immunity as well.

It has been clearly established that vaccination through mucosal routes generates both mucosal and systemic immune responses, whereas systemic routes of vaccination usually only generate systemic immunity. Mucosal immunization therefore offers advantages for vaccines against pathogens that invade through mucosal tissues, such as HIV. The ability of mucosal vaccination to also induce systemic immunity means that vaccine efficacy can also encompass host defense against disseminated pathogens. Although BCG vaccine is now given intradermally, it was given orally in past years. Recent experimental evidence, however, has thinly established that BCG can induce mucosal immunity at both local and distant sites when administered intranasally as well. Unfortunately, however, intranasally-administered BCG quickly disseminates to other tissues, even in immunocompetent mice.

Intranasal vaccination has several advantages as a site for mucosal immunization, including the ease of administration and the increasing number of demonstrations of intranasal vaccine efficacy. Most relevant to the prospect of creating effective prophylactic HIV vaccines, however, is that intranasal vaccination may be the best route for inducing immunity in the genital tract. The difficulty of inducing immune responses in genital tissues was recently reviewed in an article entitled "Immunological Uniqueness of the Genital Tract: Challenge for Vaccine Development. Citing many studies that have compared routes of vaccination, the authors conclude that "Intranasal immunization, however, appears to be the most effective route for the generation of genital tract responses in several animal models." Many additional studies could be added to those cited in the review, which further emphasize the critical point that intranasal vaccination can induce strong and durable antibody and cell-mediated immunity in vaginal, cervical, and rectal tissues, and in the ileal lymph nodes that drain these tissues.

The inability of *M. shottsii* to grow at 37° has been repeatedly confirmed, both on agar plates and in nutrient broth, even after months of incubation. For example, plating approximately $2 \times 10^7$ *M. shottsii* yielded no CFU at 37° C. The temperature growth-restriction of *M. shottsii* has been confirmed and the results are presented in Table 2.

TABLE 2

Temperature tolerance of *M. shottsii*.

|  | 22° | 26° | 29° | 37° |
|---|---|---|---|---|
| Plate cultures | +++ | +++ | + | − |
| Broth cultures | +++ | +++ | − | − |

A 0.1 ml aliquot from *M. shottii*, cultured in Middlebrook 7H9 + OADC + 0.25% Tween 80 to an OD580 = 1.0, was spread onto each of several 7H11 + OADC plates and inoculated into 15-ml culture tubes containing 2 ml of Middlebrook 7H9 + OADC + 0.25% Tween 80. Replicate plate and broth cultures were incubated stationary at multiple temperatures (22°, 26°, 29°, and 37° C.). Liquid cultures were mixed by inversion every 3-4 days.
The table represents growth observed after 30 days incubation. (+++ confluent lawn or turbid liquid culture, + minimal growth on plate, − complete absence of growth).

Research Design and Methods

Several plasmids bearing HIV gag p24 genetic sequences will be constructed, electroporated into *M. shottsii*, and the resulting strains will be assessed for the amount of HIV antigen produced. One or more engineered strains that express high levels HIV antigen will be selected as model vaccines. The HIV p24 antigen has been selected as a model antigen because of the ready availability of related reagents, and because codon optimization of the gene to increase production in BCG (or other mycobacteria, which are characterized as having very high GC genomes) has already been accomplished. Vaccines created in this example will demonstrate that a fish mycobacterium can serve as an HIV vaccine vector.

The immunogenicity of a vectored vaccine construct is expected to be positively correlated with the amount of heterologous protein expressed. In addition, there is some evidence that, in the case of intracellular bacteria such as BCG or *M. shottsii*, having the heterologous protein secreted rather than retained in the bacterial cytoplasm may be favorable for inducing immunity. Two factors that influence the amount of protein produced are the strength of the promoter used, and the extent to which the codons in the foreign DNA have been optimized to match the availability of aminoacyl tRNAs. Both of these factors will be manipulated in constructing the plasmids in Aim One. Many highly immunogenic BCG vaccine constructs have used the hsp60 promoter from *M. tuberculosis*, and this will be one of two promoters used. The second promoter used is the mycobacteriophage L5 promoter, which has been found to be more powerful than hsp60 at driving expression of a gene, including the gene for green fluorescent protein in the fluorescent strain of *M. shottsii* of Example 3. Codon optimization for enhanced expression of HIV genes in BCG is a proven strategy for increasing protein production, no doubt because 60.9% of HIV genes have either A or T in the third codon position, while 81.0% of BCG codons have either G or C in the third position. Kanekiyo and associates found that by optimizing the codons in the p24 gene for expression in BCG, the resulting recombinant BCG produced 40 fold more p24 than did a recombinant BGC containing the wild-type p24 gene sequence. This example will compare the wild-type and the codon-optimized sequences in constructing the plasmids. The final parameter that will be examined is insertion of the p24 genes behind signal sequences of proteins known to be secreted by mycobacteria. In this example, the signal sequences for beta-lactamase or for erp (external repetitive protein) will be used. All of the factors have the potential to interact synergistically to optimize antigen expression.

The HIV p24 gene optimized for expression in mycobacteria will either be obtained from Kanekiyo and colleagues (Kanekiyo et al., J. Virol. 2005; 79(14):8716-23), or synthesized and assembled by ligation of six overlapping approximately 130-nucleotide (nt) chemically synthesized oligonucleotides that incorporate the codon-optimized base changes. Restriction endonuclease sites will be engineered at the ends of the gene for directional cloning into plasmid vectors. The wild type p24 gene will be obtained by PCR from plasmid p83-2 (available through the NIH AIDS Research and Reference Reagents Program) and analyzed in parallel to the codon-optimized p24 gene. Expression of p24 will be placed downstream of the mycobacteriophage L5 promoter and ribosome binding site by cloning into plasmid pFJS8 and also behind the *M. tuberculosis* hsp60 heat shock promoter and ribosome binding site by cloning into plasmid pMV261. Both plasmids utilize the same mycobacterial origin of replication. It has been confirmed that this replicon functions in *M. shottsii* as a derivative of pFJS8 expressing green fluorescent protein yields labeled bacteria. Stability of plasmid-based expression systems in *M. shottsii* without antibiotic selection (i.e. during mouse infections) is a concern being investigated. *M. shottsii* expressing green fluorescent protein (GFP) from the mycobacteriophage L5 promoter on plasmid pFJS8, which also encodes the aph kanamycin resistance gene, has been subcultured into medium lacking kanamycin. Bacilli that lose the plasmid will be readily detectable as they will lose fluorescence when examined by fluorescence microscopically. If pFJS8GFP proves unstable without selection for 8 weeks, then the p24 expression studies will instead be constructed in plasmid pMV306, which does not replicate in mycobacteria, but encodes aph, a colE1 origin of replication, and the mycobacteriophage L5 attachment site and integration gene. This vector will be able to integrate into the chromosome of *M. shottsii* as mycobacteriophage L5 has been shown to integrate into the chromosome of both fast-growing saprophytic *M. smegmatis* and slow-growing species such as *M. bovis* BCG and *M. tuberculosis* at the mycobacteriophage L5 attachment site. *M. shottsii* was recently electroporated with pMV306 DNA and plated on selective medium. Colony PCR of kanamycin-resistant colonies will be performed to screen for the presence of the L5 integration gene.

To maximize antigen presentation, gag p24 expression will also be placed behind promoter and signal sequences of two known mycobacterial secreted proteins: *M. fortuitum* β-lactamase and *M. tuberculosis* Erp. The *M. fortuitum* blaF promoter and signal sequence have been reported to direct secretion of fusion proteins in *M. bovis* BCG. As many mycobacteria species are resistant to β-lactam antibiotics, *M. shottsii* is predicted to encode a secreted β-lactamase; resistance to β-lactam antibiotics is currently being tested. Although the full genome of *M. shottsii* has not been sequenced, partial sequence of an *M. shottsii* homolog to the exported repetitive protein, Erp, from *M. tuberculosis* has been deposited in the NCBI database (accession # AY496288). Therefore, the promoter and signal sequences for both *M. fortuitum* blaF and *M. tuberculosis* erp will be obtained by PCR from genomic DNA from each parent strain and inserted into the plasmid pMV306. The wild type and mycobacterial codon-optimized p24 genes will then be cloned in-frame behind the signal peptides of blaF or erp in the resulting plasmids.

In the unlikely event that both the self-replicating and integratable plasmids prove unusable for this study, p24 under control of the various promoters and signal sequences will be cloned onto a suicide vector containing the 361-bp *M. shottsii* erp region (NCBI accession # AY496288), which can be obtained by PCR from chromosomal DNA. The erp sequence will serve as a region of homology to direct insertion of the suicide plasmid onto the chromosome via homologous recombination methods routinely used in the mycobacterial field.

Quantification of p24 protein produced and selection of model vaccines. Each of the genetically engineered strains created will be grown in broth under standardized conditions, and the number of viable *M. shottsii* bacilli will be quantified by plating aliquots at intervals to determine colony forming units (CFU). Any recombinant strains that grow substantially slower than the parent strain will be eliminated from consideration at this time as model vaccines. It is interesting to note that very high production of a foreign protein can be toxic to the host cell, so it is possible that some constructs predicted to have maximal production of p24 may turn out to be too impaired for growth to be good vaccine candidates. Strains that are comparable in growth to the parent strain will be grown and sampled at intervals for p24 protein in the culture supernate or in the sonicate of pelleted cells. Quantification of p24 will utilize commercially available ELISA kits. Three of the best p24-producing strains will be selected to take forward into the Aim Three studies as model vaccines, and bank the others for possible future studies.

Following the procedures described in Example 1, the relative safety of *M. shottsii* to the live BCG vaccine administered intranasally to immunocompromised (SCID) mice. Briefly, for both the survival curve and the tissue dissemination studies, groups of JAX®B6.CB17-Prkdc SCID mice will be intranasally inoculated with either $10^6$ log phase BCG bacilli, $10^6$ log phase *M. shottsii* or, as the control, phosphate buffered saline (PBS). For the survival curve analysis, there will be eight mice in each group. The read-out of this assay is termed "survival time" A final statistical analysis of all three groups, using the log rank test, will be performed. If the survival curve of the *M. shottsii* mice is not statistically different from the PBS control group, this will mean that the *M. shottsii* vaccine is avirulent in a severely immunodeficient mouse model that is increasingly being accepted as predictive of safety in immunocompromised people.

For the tissue dissemination studies, there will be two mice in each experimental group (BCG, *M. shottsii* or PBS) at each of six time points, for a total of 36 SCID mice.

The ability of intranasally administered HIV-expressing *M. shottsii* vaccine to induce mucosal and systemic antigen-specific T cell responses will be measured by quantifying interferon-γ ELISPOTS produced by lymphoid cells from mouse spleen, nasal, genital and intestinal tissues. As a second measure of immunogenicity, serum and vaginal-wash antibodies specific for the p24 antigen will also be measured and isotyped. These studies will demonstrate *M. shottsii* potential as an HIV vaccine vector.

Three model vaccines will be selected from the engineered *M. shottsii* strains and used to intranasally immunize female BALB/c mice. Unvaccinated mice will serve as controls. Initially, three vaccination regimens will be compared, vaccinating once, twice or three times. For the vaccination regimens involving more than one dose, there will be an interval of two weeks between each dose. In all cases, the vaccine dose will consist of $10^6$ *M. shottsii* delivered intranasally in a volume of 10 microliters (µl).

In the first set of experiments, groups of vaccinated mice will be sacrificed at 1 month, 3 months, and 6 months, following the last intranasal dose of vaccine. Each vaccine/time point group of mice will consist of four mice, which is the minimum needed to obtain the required number of lymphoid cells from the nasal and gut tissues for the ELISPOT assays, as explained below.

For the antibody studies, protocols will closely follow those used by Hong-Yin Wu and colleagues (Wu et al., Infect Immun. 2000; 68(10):5539-45). At each time point when mice are to be euthanized for the immunological studies, they will first be anesthetized for collection of vaginal washes and venous blood from the tail vein. Samples of each type will be pooled from the four mice in each experimental group. Vaginal secretions will be collected by washing three times with 500 of PBS. All washes from the mice in each experimental/timepoint group will be pooled and stored at −20° C., so that the ELISA assays from an entire experiment can be run at the same time. Likewise, the 50-100 µl of tail vein blood from each mouse will be pooled, spun to isolate the serum, and stored at −20° C.

Antibodies specific for either p24 or for mycobacterial antigens of the *M. shottsii* vector will be captured microtiter plates coated with either p24 protein or short term culture filtrate of parental *M. shottsii* cultures. Detection of antigen-specific IgG and IgA antibodies will utilize labeled anti-mouse immunoglobulins specific for each isotype in the standard ELISA format. In addition, total (as opposed to antigen-specific) IgG and IgA immunoglobulins will be determined in the samples by standard ELISA methods, so that specific antibodies can also be expressed as a proportion of total immunoglobulin in the data analysis.

For IFN-γ-secreting ELISPOT studies, spleen, intestinal intraepithelial lymphocytes, and NALT and nasal passage tissues will be harvested and single cell suspensions will be prepared. Intestinal intraepithelial lymphocytes (TEL) will be isolated using previously published methods (Culshaw et al., Infect Immun. 1997; 65(8):3074-9), which yields about $4 \times 10^6$ TEL per mouse. Specific ELISPOT assay will be by the published methods of the same authors (Culshaw et al., Infect Immun. 1997; 65(8):3074-9). NALT and nasal passage tissues will be isolated using previously published methods (Asanuma et al., J Immunol Methods. 1997; 202(2):123-31) with an expected yield of approximately $3.1\times10^5$ NALT lymphoid cells and $6.5\times10^6$ NP cells per mouse. HIV p24 interferon-gamma ELISPOT assay will be performed using previously published methods (Kanekiyo et al., J. Virol. 2005; 79(14):8716-23). Isolating lymphoid cells, including T cells from the vaginas of mice will be previously published methods. Yield is expected to be low. About $3\times10^5$ lymphoid cells were obtained by processing and combining vaginal cells from seven mice (Dupuy et al., J. Virol. 1999; 73(11):9063-71). ELISPOT studies of vaginal lymphocytes will be performed. Stimulation of the cell suspensions will include recombinant HIV p24 antigen, short term culture filtrate proteins (representing native antigens on *M. shottsii*), Con A (nonspecifically stimulates Th1 cells), and media only.

Example 6

Influenza Vaccine

This example will develop a prototype influenza vaccine and demonstrate its safety, immunogenicity, and protective efficacy in a mouse model. The overall goal of this research is to develop a vaccine for pandemic influenza. This example will develop and test a novel influenza prototype vaccine based upon the use of the live, naturally cold-adapted mycobacterial vector *M. shotsii*. It includes four Aims.

Such an influenza vaccine could overcome obstacles facing vaccine manufacturers. Today's influenza vaccine production technology and manufacturing capacity is insufficient to supply the number of vaccine doses that would be required in a timely manner. The vaccine of the present example would be produced by essentially the same method as BCG vaccine, which is currently manufactured at more than 40 sites worldwide (Fine et al., 1999 "Issues related to the use of BCG in immunization programmes," available on the world wide web at vaccines.who.int/entity/vaccine_research/documents/en/bcg_vaccines.pdf).

A broader protective immune response would be highly desirable because the pandemic strain would undergo extensive genetic drift as it traveled through the global population, probably in a succession of waves, as did the 1918 pandemic. BCG-vectored vaccines produce strong and durable antibody responses and T cell-mediated immunity, which are believed to contribute to heterosubtypic immunity against antigenically disparate influenza strains (Liang et al., 1994 J Immunol 152: 1653-1661; and Tamura et al., Jpn J Infect Dis 58: 195-207).

Like the cold-adapted live influenza strains in FluMist®, a transgenic *M. shottsii* vaccine could be administered intranasally, a method that induces mucosal as well as systemic immunity, and that could allow vaccine self-administration in a pandemic.

Aim One will evaluate the safety, reactogenicity, dissemination, and persistence of the new vaccine vector in severely immunocompromised (SCID) mice and in immunologically normal (BALB/c) mice.

Aim Two will develop at least eight different vaccine vector constructs by inserting the influenza hemagglutinin (HA) gene into the chromosomal DNA of the mycobacterial genome, varying the promoters and signal sequences, and optimizing codon usage for synthesis in mycobacteria. The amount and functional activity of HA produced by each construct will be compared, and four constructs will be selected for more detailed study of vaccine immunogenicity.

Aim Three will test the immunogenicity of each of the four vaccine constructs for their ability to induce serum and mucosal antibody isotypes and titers, and for the induction of Th1 cell-mediated immunity. From these studies, at least two lead experimental vaccines will be taken forward into viral challenge and protection studies.

Aim Four will test the efficacy and breadth of protection conferred by immunizing groups of mice with either one or two doses of the experimental vaccines, and then challenging them after various intervals with influenza viruses containing either the same HA gene used to construct the vaccines or viruses containing HA genes with varying degrees of difference from the vaccines. The vectors of this example will induce both humoral and cell-mediated immunity in the upper respiratory mucosa and systemically and will confer strong, long-lasting, and broadly protective immunity.

Today's influenza vaccine production technology and manufacturing capacities are not up to the challenge of producing sufficient vaccine in a timely manner. Currently influenza vaccines are produced in embyonated chicken eggs, a technology that has been widely discussed as too slow. National and international authorities have called for the development of new technologies, and a number of companies and research groups are working on developing alternative approaches, such as production in mammalian cell lines, DNA vaccines, and virally-vectored vaccines (Schwartz and Gellin, JID 2005; 191:1207-1209; Kemble and Greenberg, Vaccine 2003; 21:1789-1795; and Palese, Emerg Infect Dis 2006; 12:1043). Each of these approaches has drawbacks and faces regulatory hurdles, so any reasonable alternative bears careful consideration and an opportunity to prove itself.

In this example, influenza genes will be expressed in the recently discovered mycobacterium, *M. shottsii*. *M. shottsii* is related to the live, attenuated vaccine BCG, and which could be produced by any of the more than 40 BCG vaccine production facilities throughout the world. BCG has been used as a live, attenuated vaccine against tuberculosis for over 80 years, and approximately 600 million doses are manufactured annually at a cost of pennies per dose. Production of a mycobacteria-based vaccine could utilize current BCG facilities or similar bioreactors, and would not interrupt the production of standard influenza vaccines.

Experimental Design and Methods

Aim One will evaluate the safety, reactogenicity, dissemination, and persistence of the new vaccine vector in severely immunocompromised (SCID) mice and in immunologically normal (BALB/c) mice. There will be both a short term and a long term component to these studies, which can begin concurrently. This study will use both severely immunocompromised SCID mice, which have neither T cells nor B cells to limit the growth or dissemination of bacteria, and natural BALB/c mice which will respond immunologically to the bacteria and thus show greater tissue reactogenicity. Groups of mice will be lightly anesthetized and intranasally inoculated with either $10^6$ *M. shottsii*, $10^6$ BCG, or saline (control). It has been shown that *M. shottsii* grows intracellularly in macrophages, and it is expected that *M. shottsii* bacilli, as has been shown for other mycobacteria, will also infect and replicate in dendritic and epithelial cells. To assess the persistence of viable mycobacteria, tissue homogenates will be cultured from lymphoid organs or tissues where lymphoid cells cluster, as these areas will contain macrophages and dendritic cells that could be infected with *M. shottsii* or the positive control mycobacterium BCG. In the upper respiratory tissues, a dense fabric of dendritic cells underlies the epithelial cell layer everywhere along the airways. These dendritic cells sample inhaled antigens and direct the immune response. In the mouse nasopharynx and oropharynx, the organized lymphoid tissues to be dissected in our study include the nasal-associated lymphoid tissue (NALT), and additional lymphoid tissues in the nose, including the nasal turbinates, septum, and lateral nasal passage walls. These are superficial mucosal tissues that are likely to be substantially cooler than mouse body temperature, and most permissive for the growth of *M. shottsii*. *M. shottsii* persistence and growth in these tissues will be documented, at least over a period of weeks, as this is expected to induce a strong immune response and the development of memory B cells and T cells (Kyd et al., Vaccine. 2001; 19(17-19):2527-33; Davis, Adv Drug Deliv Rev. 2001; 51(1-3):2'-42; Illum and Davis, Adv Drug Deliv Rev. 2001; 51(1-3):1-3; Zuercher et al., J. Immunol. 2002; 168(4):1796-803; Porgador et al., Infect Immun. 1998; 66(12):5876-81). Lying deeper in the tissues (and hence warmer) are the cervical, submandibular, palatine, and tracheobronchial lymph nodes (a double chain of lymph nodes located along the trachea and bronchi), which drain the nasopharyngeal, oropharyngeal, and tracheal tissues. Published methods for dissecting and dissociating the cells from these lymph nodes, and from the NALT and nasal passage tissues are available.

To assess the ability of *M. shottsii* to disseminate to internal organs, the lungs, spleens and livers will be examined and cultured, as these are the organs in which *M. tuberculosis* and BCG grow in great numbers. These studies are a critical test of our hypothesis that the temperature sensitivity of *M. shottsii*, like that of cold-adapted viruses, will keep it confined to the superficial tissues of the upper respiratory tract.

Tissues will be aseptically dissected. A portion will be cultured. The remaining tissue will be examined for signs of tissue reactogenicity, such as inflammation or a granulomatous response.

The long teen component of these studies will use a SCID mouse model. Survival curves will be compared in SCID mice intranasally inoculated, with either *M. shottsii*, BCG, or saline, as described above, using eight mice in each group. It is expected that the BCG inoculated mice will succumb between 8 and 11 weeks after inoculation (Sambandamurthy et al., Nat. Med. 2002; 8(10):1171-4). Group sizes are powered for comparison of survival curves, which will be compared using the log rank test (Bland and Altman, BMJ 2004; 328 bmj.com; and Bland and Altman, BMJ 11998; 317: 1572-1580. bmj.com). The first log rank analysis will be conducted when the BCG injected mice have succumbed, and will be used to test the null hypothesis that there is no difference between the survival curves of the BCG and *M. shottsii* inoculated mice. Note that the log rank test, like the Kaplan-Meier method, is appropriate to use when some individuals have not yet died (in statistical terms, some survival times are censored). If no significant difference is found between the BCG and *M. shottsii* survival curves, this will mean that *M. shottsii* is as attenuated as BCG in this model. If the *M. shottsii* inoculated mice survive longer than the BCG inoculated mice, and the survival curves are clearly different for this reason, this will mean that *M. shottsii* is more attenuated than BCG in this model. The *M. shottsii* and saline inoculated groups will be followed for as long as the *M. shottsii* inoculated mice survive, up to a maximum of 270 days post-inoculation. A final statistical analysis of all three groups, using the log rank test, will be performed. If the survival curve of the *M. shottsii* mice is not statistically different from the saline control group, this will mean that *M. shottsii* is avirulent in a severely immunodeficient mouse model that is increasingly being accepted as predictive of safety in immunocompromised people.

Aim Two will develop at least eight different vaccine vector constructs by inserting the influenza hemagglutinin (HA) gene into the chromosomal DNA of the mycobacterial genome, varying the promoters and signal sequences, and optimizing codon usage. The amount, functional activity, and antigenicity of HA produced by each construct will be compared, and four constructs will be selected for more detailed study of vaccine immunogenicity.

For budgetary reasons, only the HA gene of influenza will be inserted into the *M. shottsii* genome to create a prototype influenza vaccine. Studies using separate plasmids containing each of the influenza genes have shown that immunization with HA alone is sufficient to induce protective immunity in mice (Chen et al., Jpn J Infect Dis 53: 219-228). A great advantage of a bacterial vector, as apposed to a viral vector, is that there is almost no limit to the foreign genetic material that the vector can carry. It is entirely feasible to clone all of the genes in influenza into *M. shottsii*, including genes encoding the very interesting and conserved internal proteins. The HA gene from the strain A/Fujiian/411/02 will be utilized to construct our vaccine candidates because a series of genetically drifted strains are available for the challenge studies in Aim Four. The immunogenicity of a vectored vaccine construct is generally positively correlated with the amount of heterologous protein expressed. Two factors that influence the amount of protein produced are the strength of the promoter used, and the extent to which the codons in the foreign DNA have been optimized to match the availability of aminoacyl tRNAs. Both of these factors will be manipulated in constructing the plasmids to be electroporated into *M. shottsii* in Aim Two. Many highly immunogenic BCG vaccine constructs have used the hsp60 promoter from *M. tuberculosis*, and this will be one of two promoters that will be used. The second promoter that will be used is the mycobacteriophage L5 promoter, which is more powerful than hsp60 at driving expression of a gene, including the gene for green fluorescent protein in the fluorescent strain of *M. shottsii* described in Example 3. Codon optimization for enhanced expression of HIV genes in BCG is a proven strategy for increasing protein production, no doubt because approximately 80% of mycobacterial codons have either G or C in the third position. For example, Kanekiyo and associates found that by optimizing the codons in the HIV p24 gene for expression in BCG, the resulting recombinant BCG produced 40 fold more p24 than did a recombinant BGC containing the wild-type p24 gene sequence (Kanekiyo et al., J. Virol. 2005; 79(14):8716-23). In this example, the wild-type and the codon-optimized sequences will be compared in constructing our plasmids. Another factor that may affect the immunogenicity of a foreign antigen expressed by a bacterial vector is whether it is secreted, incorporated into the cell wall, or retained in the cytoplasm. By placing the HA gene behind an appropriate signal sequence, constructs will be arranged exploring all of these variables in *M. shottsii*, using known techniques.

Each of the genetically engineered strains created will be grown in broth under standardized conditions, and the number of viable *M. shottsii* bacilli will be quantified by plating aliquots at intervals to determine colony forming units (CFU). Any recombinant strains that grow substantially slower than the parent strain will be eliminated from consideration at this time as model vaccines. It is interesting to note that very high production of a foreign protein can be toxic to the host cell, so it is possible that some constructs predicted to have maximal production of HA may turn out to be too impaired for growth to be good vaccine candidates. Strains that are comparable in growth to the parent strain will be grown and sampled at intervals for HA protein in the culture supernatant or in the sonicate of pelleted cells. Quantification of HA will utilize Western blots, the traditional single radial immunodiffusion (SRID) test, and ELISA assays. The functionality of the recombinant HA will be assessed by assaying its ability to agglutinate erythrocytes and chick cells (CCA). Four of the best HA-producing strains will be selected to take forward into the Aim Three studies as model vaccines, and bank the others for possible future studies.

Aim Three will test the immunogenicity of each of the four vaccine constructs for their ability to induce serum and mucosal antibody isotypes and titers, and for the induction of Th1 cell-mediated immunity. From these studies, at least two lead experimental vaccines will be taken forward into viral challenge and protection studies.

Groups of BALB/c mice will be intranasally immunized either once or twice with the four most promising candidate vaccines developed in Aim Two. At intervals of one month, two months, and six months after vaccination, mice will be euthanized. Serum, nasal washes, and bronchoalveolar lavage fluids will be collected, and assayed for total and isotypic HA-specific antibodies by ELISA (Takada et al., Vaccine 21: 3212-3218; and Kida et al., Virology 122: 38-47). The virus neutralizing activity of antibodies in serum, nasal washes, and bronchoalveolar washes will be measured by plaque-reduction on Madin-Darby canine kidney (MDCK) cells (Takada et al., Vaccine 21: 3212-3218). Tissue homogenates will be prepared from the spleens, nasal lymphoid tissues, and the bronchial lymph nodes, and stimulated with HA antigen. Flow cytometry will be used to quantify CD4 and CD8 T cells staining for intracellular interferon gamma. These data will be used to select the two most immunogenic candidate vaccines to take forward into the protection studies in Aim Four.

Aim Four will test the efficacy and breadth of protection conferred by immunizing groups of mice with either one or two doses of the experimental vaccines, and then challenging them after various intervals with influenza viruses containing either the same HA gene used to construct the vaccines or viruses containing HA genes with varying degrees of difference from the vaccines. The ability of the unique mycobacterial vector to induce both humoral and cell-mediated immunity in the upper respiratory mucosa and systemically will confer strong, long-lasting, and broadly protective immunity.

Mice will be inoculated with either an *M. shottsii*-based vaccine or saline. For the vaccination regimens involving two doses, the doses will be given three weeks apart. Mice will be challenged intranasally with 20 times the mouse infectious dose ($MID_{50}$) of each viral strain. Challenge with the strain A/Fujiian/411/02 will assess protection from a strain with an HA identical to the vaccine strain. Challenge with A/Panama/2007/99 will assess subtypic protection from a genetically distinct H3N2 influenza strain. Challenge with A/Puerto Rico/8/34, which is an H1N1 virus, will assess heterosubtypic immunity. Groups of mice will be challenged either one week or two months after vaccination, and protection will be measured by determining viral titers in lung tissue four and seven days later, after the manner of Takada and associates (Takada et al., Vaccine 21: 3212-3218). Viral titers are calculated as $log_{10}$ plaque-forming units on MDCK cells per gram of mouse lung tissue.

These studies, if successful, may lead to a highly novel way to induce broadly protective defenses against influenza, using a vaccine that can be rapidly and inexpensively manufactured.

Example 5

A Vector for Veterinary Vaccines

Application to Influenza in Swine

In this example the live vaccine vector *M. shottsii* will be modified to induce immune responses against various veterinary diseases. Because this vector, which is a naturally cold-adapted mycobacterium isolated from fish, is intended for intranasal vaccination, it is expected to induce mucosal as well as systemic immunity. Swine influenza, an emerging illness causing significant economic losses to pork producers, has been selected as the first target disease for which to develop and test a candidate vaccine. This example will demonstrate that the vector is apathogenic in mammals, engineer the vector to express the influenza type 3 hemagglutinin gene, and confirm that intranasal vaccination with the modified vector can induce antibodies to hemagglutinin.

*M. shottsii*, engineered to express appropriate pathogen antigens, can form the basis of any number of veterinary vaccines. This naturally cold-adapted organism, like the cold-adapted influenza strains in FluMist®, can be administered intranasally, where it would only be able to persist in the superficial upper respiratory tissues. Intranasally administered *M. shottsii*-vectored vaccines are expected to induce both mucosal and systemic immunity. Because the vaccine antigens would be expressed intracellularly, *M. shottsii*-vectored vaccines are also expected to induce both cell-mediated and antibody-mediated (humoral) immunity. These attributes lead to the selection of swine influenza (SIV) as the initial veterinary disease vaccine application.

This example will validate the safety and efficacy of the vaccine vector and lead to the development of an improved SIV vaccine. Three Aims will be addressed.

Aim One will verify that the live vaccine vector is apathogenic in mammals by evaluating the safety, reactogenicity, dissemination, and persistence of the new vaccine vector in severely immunocompromised (SCID) mice and in immunologically normal (BALB/c) mice.

Aim Two will demonstrate that the influenza hemagglutinin (HA) gene can be efficiently expressed in *M. shottsii*.

Aim Three will demonstrate that the hemagglutinin expressed by the *M. shottsii*-vectored vaccine prototype is immunogenic by measuring systemic and mucosal antibody responses in immunized mice.

The importance of the problem of SIV to pork producers is considerable, and is growing in both magnitude and complexity. Influenza was first detected in swine in 1930, and for the next 40 years the only viral subtype isolated was an H1N1 strain. In 1970, a human-type H3N2 type was identified in pigs, which has since become endemic, along with the original H1N1, and more recently a reassortment virus of the H1N2 type. At the present time, it is believed that virtually all U.S. swine herds are infected with one or more influenza strains, and aggressive vaccination strategies are required to even partially control the economic losses associated with swine influenza. See, for example, Webby, "Recent reassortment and evolution of swine and human influenza viruses," available on the worldwide web at x13.info/scientific_articles/index.htm, 2002; Wuethrich, Science 2003; 299 (5612):1502-1505); and Janke, "Swine influenza and porcine respiratory disease complex," available on the worldwide web at x13.info/scientific_articles/index.htm, 2002.

Swine influenza causes anorexia, with resulting poor weight gain and inefficient feed conversion. It also causes pneumonia, either alone or in mixed pathogen infections termed Porcine Respiratory Disease Complex. Pneumonia is a cause of significant morbidity and mortality in pigs of all ages; in pregnant sows, abortions and poor fecundity are also sequellae. One hypothesis for the key role of the influenza virus in the mixed infections of Porcine Respiratory Disease Complex is that the infection and destruction of respiratory epithelial cells by the influenza virus renders the host susceptible to subsequent co-infection by pathogens that are endemic in the environment. Thus an improved swine influenza vaccine that could induce sufficient mucosal immunity to prevent the initial destruction of upper respiratory epithelium could reduce the disease burden of influenza alone and in combination infections.

*M. shottsii* as a member of the *Mycobacterium tuberculosis* complex. The *Mycobacterium tuberculosis* complex is a phylogenetic grouping that includes BCG, which is an attenuated strain of *M. bovis* that is used both as a vaccine for TB and as a vaccine vector. BCG is highly immunogenic and acts as an adjuvant, due largely to its lipid structure, and this property has been exploited to produce a number of experimental vaccines, some of which are currently in clinical trials. BCG organisms engineered to express foreign antigens from HIV, malaria, schistosomiasis, and other pathogens have proven to induce strong foreign antigen-specific T cell responses, neutralizing antibody responses, and exceptionally durable immunity (Barletta et al., Res Microbiol. 1990; 141(7-8):931-9; Fuerst et al., Biotechnol Ther. 1991; 2(1-2):159-78; Stover et al., Nature. 1991; 351(6326):456-60; Aldovini and Young, Nature 1991; 351(6326):479-82; Winter et al., Gene. 1991; 109(1):47-59; Barletta et al., Res Microbiol. 1990; 141(7-8):931-9; Fuerst et al., Biotechnol Ther. 1991; 2(1-2):159-78; Stover et al., Nature 1991; 351(6326):456-60; Aldovini and Young, Nature 1991; 351(6326):479-82; and Winter et al., Gene. 1991; 109(1):47-59). As demonstrated in Example 3, *M. shottsii* can be engineered to express foreign genes and, thus, can serve as a vaccine vector. Because of the very great lipid similarity between BCG and *M. shottsii*, it is likely that genetically engineered *M. shottsii*-based vaccines will, like BCG, induce strong and durable responses involving both antibody- and cell-mediated immunity.

Why haven't live cold-adapted influenza viruses been utilized as vaccines for swine influenza? The answer lies in the nearly unique capacity of swine to serve as reassortment vessels for multiple avian and mammalian strains of influenza (Webby, "Recent reassortment and evolution of swine and human influenza viruses," available on the world wide web at x13.info/scientific_articles/index.htm, 2002; Wuethrich, Science 2003; 299:1502-1505; Brown, Vet Microbiol. 2000; 74: 29-46; and Bridges, "Human influenza viruses and the potential for inter-species transmission," available on the worldwide web at x13.info/scientific_articles/index.htm). Co-infection of pigs with avian and human viruses is one of the mechanisms by which a potentially pandemic reassorted influenza strain could be unleashed, and therefore vaccination of swine with live influenza viruses of any sort has been considered to be risky (Wuethrich, Science 2003; 299:1502-1505; Bridges, "Human influenza viruses and the potential for inter-species transmission," available on the worldwide web at x13.info/scientific_articles/index.htm). In contrast, immunization with an *M. shottsii* strain expressing only the coding sequence from a hemagglutinin gene, without the flanking sequences that facilitate recombination, would convey little or no risk of reassortment occurring. In future vaccine prototypes, we will further reduce the influenza genetic material to key epitopes, and change the nucleic acid sequences to codons optimized for transcription by mycobacteria.

All current swine influenza vaccines consist of killed influenza viruses, and like most killed vaccines, they have the drawback of inducing only short-lived immunity. Significant decreases in antibody titers have been reported within 60 days of vaccination. An additional drawback of killed vaccines is that they induce only antibodies, and not cell-mediated immunity. While antibodies alone can be protective against influenza infection, cell-mediated immunity speeds recovery and provides a broader immunity that can protect against influenza strains not well matched to the vaccine strain. A major problem with the current killed virus vaccine is that maternal antibodies, even low titers (1:10) that are no longer protective, can prevent the successful immunization of piglets. Researchers are examining new vaccine strategies that may overcome the maternal antibody problem, such as DNA vaccination or using a viral vaccine vector. These approaches, like the use of the intracellular vector *M. shottsii*, should succeed because the recombinant antigen is synthesized within cells and displayed on their surface, rather than circulating outside of cells where maternal antibody can bind up much of the vaccine antigen.

One important point from the literature on SIV that supports our approach is the fact that pigs can be successfully immunized against swine influenza through the intranasal route of vaccination (Lim, Jap J Vet Res 2001; 48:197-203). Intranasal vaccination is the best way to induce mucosal immunity in the respiratory tissues that are the site of initial influenza virus infection. A second appeal of intranasal vaccination for pork producers is that it eliminates the risk of broken needles in meat (Warren, "Modern SIV vaccination strategies," available on the world wide web at x13.info/scintific_articles/index.htm).

Aim One will evaluate the safety, reactogenicity, dissemination, and persistence of the new vaccine vector in severely immunocompromised (SCID) mice and in immunologically normal (BALB/c) mice. There will be both a short term and a long term component to these studies, which can begin concurrently. The short term studies will use both severely immunocompromised SCID mice, which have neither T cells nor B cells to limit the growth or dissemination of bacteria, and normal BALB/c mice which will respond immunologically to the bacteria and thus show greater tissue reactogenicity. Groups of mice will be intranasally inoculated with either $10^7$ *M. shottsii*, $10^7$ BCG, or saline (control). The procedure involves placing 10 microliters of liquid on the external nares, and allowing the mice to inhale it naturally. This method does not require anesthesia. To assess the persistence of viable mycobacteria, tissue homogenates will be cultured from lymphoid organs or tissues where lymphoid cells cluster, as these areas will contain macrophages and dendritic cells that could be infected with *M. shottsii* or the positive control mycobacterium BCG. In the upper respiratory tissues, a dense fabric of dendritic cells also underlies the epithelial cell layer everywhere along the airways, where they sample inhaled antigens and direct the immune response. In the mouse nasopharynx and oropharynx, the organized lymphoid tissues to be dissected in our study include the nasal-associated lymphoid tissue (NALT), and additional lymphoid tissues in the nose, including the nasal turbinates, septum, and lateral nasal passage walls. These are superficial mucosal tissues that are likely to be substantially cooler than mouse body temperature, and most permissive for the growth of *M. shottsii*. *M. shottsii* persistence and growth in these tissues will be documented, at least over a period of weeks, as this is expected to induce a strong immune response and the development of memory B cells and T cells. Lying deeper in the tissues (and hence warmer) are the cervical, submandibular, palatine, and tracheobronchial lymph nodes (a double chain of lymph nodes located along the trachea and bronchi), which drain the nasopharyngeal, oropharyngeal, and tracheal tissues. Following previously published methods, cells from these lymph nodes and from the NALT and nasal passage tissues will be dissected and dissociated.

The internal organs that will be examined for the presence of *M. shottsii* are the lungs, spleen and liver, as these are the organs in which *M. tuberculosis* and BCG grow in great numbers. Any evidence that we obtain that *M. shottsii* can disseminate to and survive in these organs will disprove our hypothesis that the temperature sensitivity of *M. shottsii* will keep it confined to the superficial tissues of the upper respiratory tract. Following humane euthanasia with $CO_2$, tissues will sterilely dissect the tissues, a portion sent for culture, and the remaining tissue examined for signs of tissue reactogenicity, such as inflammation or a granulomatous response.

The long term component of these studies will use a SCID mouse model. Survival curves will be compared in SCID mice intranasally inoculated with either *M. shottsii*, BCG, or saline, as described above, using eight mice in each group. It is expected that the BCG inoculated mice will succumb between 8 and 11 weeks after inoculation. Group sizes are powered for comparison of survival curves, which will be compared using the log rank test. The first log rank analysis will be conducted when the BCG injected mice have succumbed, and will be used to test the null hypothesis that there is no difference between the survival curves of the BCG and *M. shottsii* inoculated mice. Note that the log rank test, like the Kaplan-Meier method, is appropriate to use when some individuals have not yet died (in statistical terms, some survival times are censored). No significant difference between the BCG and *M. shottsii* survival curves meana that *M. shottsii* is as attenuated as BCG in this model. If the *M. shottsii* inoculated mice survive longer than the BCG inoculated mice, and the survival curves are clearly different for this reason, this will mean that *M. shottsii* is more attenuated than BCG in this model. The *M. shottsii* and saline inoculated groups will be followed for as long as the *M. shottsii* inoculated mice survive, up to a maximum of 270 days post-injection. A final statistical analysis of all three groups, using the log rank test, will be performed. If the survival curve of the *M. shottsii* mice is not statistically different from the saline control group, this will mean that *M. shottsii* is avirulent in a severely immunodeficient mouse model.

Aim Two will demonstrate that the influenza hemagglutinin (HA) gene can be efficiently expressed in *M. shottsii*. The HA gene of influenza will be inserted into the *M. shottsii* genome to create a prototype influenza vaccine. Studies using separate plasmids containing each of the influenza genes have shown that immunization with HA alone is sufficient to induce protective immunity in mice. A great advantage of a bacterial vector, as opposed to a viral vector, is that there is almost no limit to the foreign genetic material that the vector can carry. It is entirely feasible to clone all of the genes in influenza into *M. shottsii*, including genes encoding the very interesting and conserved internal proteins. The HA gene from the strain A/Fujiian/411/02 (an H3N2 subtype) will be utilized to construct our vaccine candidates because a series of genetically drifted strains are available for future challenge studies that could examine the ability of the vaccine to induce heterosubtypic immunity.

The immunogenicity of a vectored vaccine construct is generally positively correlated with the amount of heterologous protein expressed. The amount of protein produced is influenced by the strength of the promoter driving expression of the gene. Most recombinant BCG-vectored vaccines have used the hsp60 promoter. Instead, the mycobacteriophage L5 promoter will be used, which has been found to be even more powerful than Hsp60 at driving expression of a gene, including the gene for green fluorescent protein in our fluorescent strain of *M. shottsii* mentioned earlier. The recombinant strain will be grown and sampled at intervals for HA protein in the culture supernatant and also in the sonicate of pelleted cells. Quantification of HA will utilize Western blots, the traditional single radial immunodiffusion (SRID) test, and ELISA assays. The functionality of the recombinant HA will be assessed by assaying its ability to agglutinate erythrocytes and chick cells (CCA). If HA gene expression or growth of the recombinant *M. shottsii* made with the L5 promoter are not satisfactory, the more traditional Hsp60 promoter will be used to drive expression of the HA gene.

Aim Three will demonstrate that the hemagglutinin expressed by the *M. shottsii*-vectored vaccine prototype is immunogenic by measuring systemic and mucosal antibody responses in immunized mice. Groups of BALB/c mice will be intranasally immunized either once or twice with the candidate vaccine developed in Aim Two. At intervals of one month and three months after vaccination, mice will be euthanized. Serum, nasal washes, and bronchoalveolar lavage fluids will be collected, and assayed for total and isotypic HA-specific antibodies by ELISA. The virus neutralizing activity of antibodies in serum, nasal washes, and bronchoalveolar washes will be measured by plaque-reduction on Madin-Darby canine kidney (MDCK) cells (Takada et al., Vaccine 21: 3212-3218).

Aim One studies are expected to find widespread dissemination of BCG, especially in the SCID mice, while finding *M. shottsii* only in the very superficial tissues of the nasopharynx. In Aim Two, significant quantities of HA are expected in sonicated cells, but possibly not in the supernate of cultures. With Aim Three, detecting at least serum IgG antibodies to HA is expected, but detecting mucosal antibodies may prove more difficult for technical reasons.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

For any method disclosed herein that includes discrete steps, the steps may be conducted in any feasible order. And, as appropriate, any combination of two or more steps may be conducted simultaneously.

What is claimed is:

1. A pharmaceutical composition comprising *Mycobacterium shottsii* and a pharmaceutically acceptable carrier, wherein the pharmaceutical composition is certified bovine spongiform encephalopathy (BSE)-free.

2. The pharmaceutical composition of claim 1 formulated for administration to the mucosa.

3. The pharmaceutical composition of claim 1 formulated for intradermal, intranasal, intramuscular, or subcutaneous administration.

4. The pharmaceutical composition of claim 1, wherein the pharmaceutically acceptable carrier is pyrogen free.

5. The pharmaceutical composition of claim 1, wherein the *Mycobacterium shottsii* (*M shottsii*) comprises at least one heterologous antigen and/or immunogen, wherein the at least one heterologous antigen and/or immunogen is encoded by a vector that replicates extra-chromosomally or is integrated into the mycobacterial chromosome.

6. The pharmaceutical composition of claim 1 further comprising an adjuvant.

7. The pharmaceutical composition of claim 1, wherein the *Mycobacterium shottsii* has not genetically modified by human genetic manipulation.

8. A method of inducing an immune response in a mammalian subject, the method comprising administering a pharmaceutical composition of claim 1 to the mammalian subject.

9. The method of claim 8 wherein the pharmaceutical composition is administered to the subject's mucosa.

10. The method of claim 8 wherein the pharmaceutical composition is administered intradermally, intranasally, intramuscularly, or subcutaneously.

11. The method of claim 8 wherein the mammalian subject is immunocompromised.

12. The method of claim 8 wherein the administration induces in the mammalian subject a positive cutaneous delayed type hypersensitivity (DTH) reaction to PPD and/or antibodies to one or more antigens in the tuberculosis antigen 85 complex.

13. A composition comprising *Mycobacterium shottsii*, wherein the composition is certified bovine spongiform encephalopathy (BSE)-free.

14. The composition of claim 13, wherein the *Mycobacterium shottsii* (*M shottsii*) comprises at least one heterologous antigen and/or immunogen, wherein the at least one heterologous antigen and/or immunogen is encoded by a vector that replicates extra-chromosomally or is integrated into the mycobacterial chromosome.

15. The composition of claim 13, wherein the *Mycobacterium shottsii* has not been genetically modified by human genetic manipulation.

16. A method of inducing an immune response in a mammalian subject, the method comprising administering a pharmaceutical composition of claim 13 to the mammalian subject.

17. A composition comprising *Mycobacterium shottsii*, wherein the *Mycobacterium shottsii* has been cultured only with certified bovine spongiform encephalopathy (BSE)-free materials.

18. The composition of claim 17 further comprising an adjuvant.

19. The composition of claim 17 formulated for administration to the mucosa.

20. The composition of claim 17 formulated for intradermal, intranasal, intramuscular, or subcutaneous administration.

21. The composition of claim 17, wherein the *Mycobacterium shottsii* (*M shottsii*) comprises at least one heterologous antigen and/or immunogen, wherein the at least one heterologous antigen and/or immunogen is encoded by a vector that replicates extra-chromosomally or is integrated into the mycobacterial chromosome.

22. The composition of claim 17, wherein the *Mycobacterium shottsii* has not genetically modified by human genetic manipulation.

23. A method of inducing an immune response in a mammalian subject, the method comprising administering a composition of claim 17 to the mammalian subject.

* * * * *